United States Patent [19]

Morland et al.

[11] Patent Number: 4,576,629

[45] Date of Patent: Mar. 18, 1986

[54] HERBICIDAL THIADIAZOLE UREAS

[75] Inventors: Robert B. Morland; Anson R. Cooke, both of Durham, N.C.; John R. Bishop, Hatfield, Pa.

[73] Assignee: Union Carbide Corporation, Danbury, Conn.

[21] Appl. No.: 589,724

[22] Filed: Mar. 15, 1984

[51] Int. Cl.$^4$ ............................................. A01N 43/02
[52] U.S. Cl. ........................................ 71/90; 548/140; 546/175; 544/224
[58] Field of Search ................... 548/140; 546/175; 544/224; 71/90

[56] References Cited

U.S. PATENT DOCUMENTS

| | | | |
|---|---|---|---|
| 3,929,816 | 12/1975 | Rathgeb et al. | 548/140 |
| 3,931,209 | 1/1976 | Krenzer | 548/140 |
| 3,932,437 | 1/1976 | Doyle, Jr. et al. | 548/140 |
| 4,056,382 | 1/1977 | Soper | 548/140 |
| 4,066,436 | 1/1978 | Kirkpatrick | 71/90 |
| 4,073,793 | 2/1978 | Arndt et al. | 548/140 |
| 4,175,081 | 11/1979 | Driscoll | 548/140 |
| 4,182,712 | 1/1980 | Driscoll | 548/140 |
| 4,217,459 | 8/1980 | Kirkpatrick | 548/140 |
| 4,239,524 | 12/1980 | Nusslein et al. | 548/140 |

OTHER PUBLICATIONS

*Chemical Abstracts:* vol. 88 (21) 147495r (1978), Selective Herbicide Composition for Use in Soya Bean Cultivation: Kirkpatrick J. L.
*Chemical Abstracts* 88 (21) 147497t (1978).
*Chemical Abstracts* 74(3) 13162g (1971): 1,3,4--Thiadiazol-5-yl Ureas: Metzger et al, Geoffen 1,816,568.

*Primary Examiner*—Paul R. Michl
*Assistant Examiner*—Alex H. Walker
*Attorney, Agent, or Firm*—Clement J. Vicari

[57] ABSTRACT

Herbicidal thiadiazole ureas are provided wherein the 5-position of the thiadiazole ring is hetero substituted and which exhibit enhanced selective herbicidal activity.

28 Claims, No Drawings

HERBICIDAL THIADIAZOLE UREAS

FIELD OF THE INVENTION

This invention relates to thiadiazole urea compounds, herbicidal compositions containing such compounds, a process for the preparation of such compounds and methods of using such compounds.

BACKGROUND OF THE INVENTION

Phenyl ureas such as N'-3,4-dichlorophenyl-N,N-dimethyl-urea are known to possess herbicidal activity. However, the very broad spectrum herbicidal activity of these known phenyl ureas imposes severe limitations on the practical use of these compounds due to their lack of selectivity and potential injury to important crops such as corn and soybeans.

SUMMARY OF THE INVENTION

This invention relates to novel thiadiazole ureas that show unexpectedly high and/or unexpectedly selective herbicidal activity. This invention also relates to herbicidal compositions containing thiadiazole ureas, methods of using such compounds and a process for preparing such compounds.

DETAILED DESCRIPTION OF THE INVENTION

The thiadiazole ureas of this invention have the following structural formula:

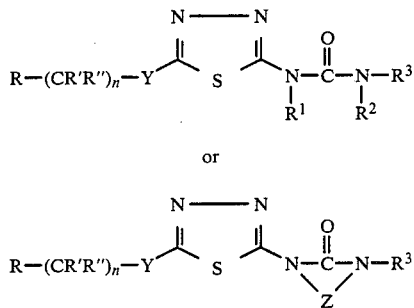

wherein:
R is:
(a) a substituted or unsubstituted radical having the structural formula:

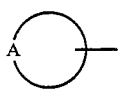

wherein A is an alkylene or alkenylene chain having 5, 6 or 7 ring members which may be replaced by up to three hetero atoms, in any location and in any combination, selected from the groups of oxygen, nitrogen and sulfur or A is a six-membered polyunsaturated carbon chain forming a phenyl ring. wherein the permissible substituents are one or more alkyl, alkoxy, carboalkoxy, monoalkylamino, dialkylamino, amido, alkylthio, phenyl, halogen, trihalomethyl, hydroxy, cyano, mercapto or nitro substituents provided that any substituent may not have more than eight aliphatic carbon atoms; or (b) a substituted or unsubstituted radical having the structrual formula:

wherein A is as defined above and A' is an alkylene or alkenylene chain having 3, 4 or 5 members which may be replaced by up to three hetero atoms, in any location and in any combination, selected from the group of oxygen, nitrogen and sulfur or A' is a 4-membered polyunsaturated chain, wherein the permissible substituents are one or more alkyl, alkoxy, carboalkoxy, monoalkylamino, dialkylamino, amido, alkylthio, phenyl, halogen, trihalomethyl, hydroxy, cyano, mercapto or nitro substituents; or (c) a substituted or unsubstituted alicyclic alkyl radical wherein the permissible substituents are one or more alkyl, alkoxy, carboalkoxy, monoalkylamino, dialkylamino, amido, alkylthio, phenyl, halogen, trihalomethyl, hydroxy, cyano, mercapto or nitro substituents; provided that R may not contain more than 12 aliphatic carbon atoms;

R' and R" are independently hydrogen, alkyl, cycloalkyl, alkoxy, carboalkoxy or halogen provided that R' and R" independently may contain no more than four carbon atoms;

Y is oxygen, alkylamino ($C_1$-$C_8$), or, when R is other than phenyl or naphthyl, Y may additionally be sulfur, sulfinyl or sulfonyl;

n is an integer from 1 to 5;

$R^1$, $R^2$ and $R^3$ are independently hydrogen, alkyl, cyclopentyl, cyclohexyl, phenyl or alkyl or alkoxy, each containing no more than eight carbon atoms; and Z is a substituted or unsubstituted divalent alkylene or alkenylene chain, having two or three chain members wherein any one carbon atom in said chain may be replaced with an amino-group and any one or two carbon atoms in said chain may be replaced with a carbonyl-group and wherein the permissible substituents are one or more halo, hydroxy or alkoxy.

When A or A' do not contain a hetero atom as a ring member, R is a carbocyclic group such as phenyl, naphtyl or cyclohexyl. When R is heterocyclic, the heterocyclic radical must contain at least one heteroatom but may not contain more than 3 heteroatoms per ring. The heterocyclic radical must include a heterocyclic ring having at least 5 but no more than 7 ring members. Examples of suitable heterocyclic radicals are pyrrolyl, furanyl, thienyl, indolyl, benzofuranyl, benzo[b]thienyl, isoindolyl, isobenzofuranyl, benzo[c]thienyl, pyridinyl, pyranyl, quinolinyl, isoquinolinyl, pyrazolyl, imidazolyl, imidazolidonyl, isoxazolyl, oxazolyl, isothiazolyl, thiazolyl, imidazolinyl, 1,2-dithiolyl, 1,3-dithiolyl, 1,3-oxathiolyl, 1,3-dioxyolyl, 1,3-dioxolanyl, pyridazinyl, pyrimidinyl, pyrazinyl, 2H-1,2-oxazinyl, 2H-1,3-oxazinyl, 4H-1,4-oxazinyl, 1,2-dioxanyl, tetrahydrofuranyl, 1,3-oxathianyl, 1,4-dithianyl, 1,3-dithianyl, purinyl, 1,3,5-triazinyl, benzotriazolyl, 1,2,3-oxadiazolyl, 1,2,4-oxadiazolyl, 1,3,4-thiadiazolyl benzoxazolyl, benzothiazolyl, quinoxazolinyl, phthalimidyl, and succinimidyl.

Z is a divalent chain which may be simple alkylene (e.g. —$CH_2$—$CH_2$—) simple alkenylene (e.g. —CH=

CH—), alkylene substituted with halo, hydroxy or alkoxy (e.g. —CH$_2$—CHCl—, —CH$_2$—CHOH— and —CH$_2$—CHC(OCH$_3$)—) or which may be more a complex chain having carbonyl or amino moieties (e.g. —CH$_2$—CO—, —CO—CO—, —CH$_2$—NH—, —CH$_2$—NCH$_3$— and —CO—NH—).

The preferred compounds are those wherein R is heteroaryl such as thienyl, isoxazolyl, pyridinyl, or 1,3,4-thiadiazolyl, R' and R" are hydrogen, n is 1 or 2, A is sulfur and (a) R$^1$ and R$^2$ are methyl and R$^3$ is hydrogen or methyl or (b) Z is —CH$_2$—CHOH—.

The thiadiazole urea compounds of this invention can be prepared by the following general methods.

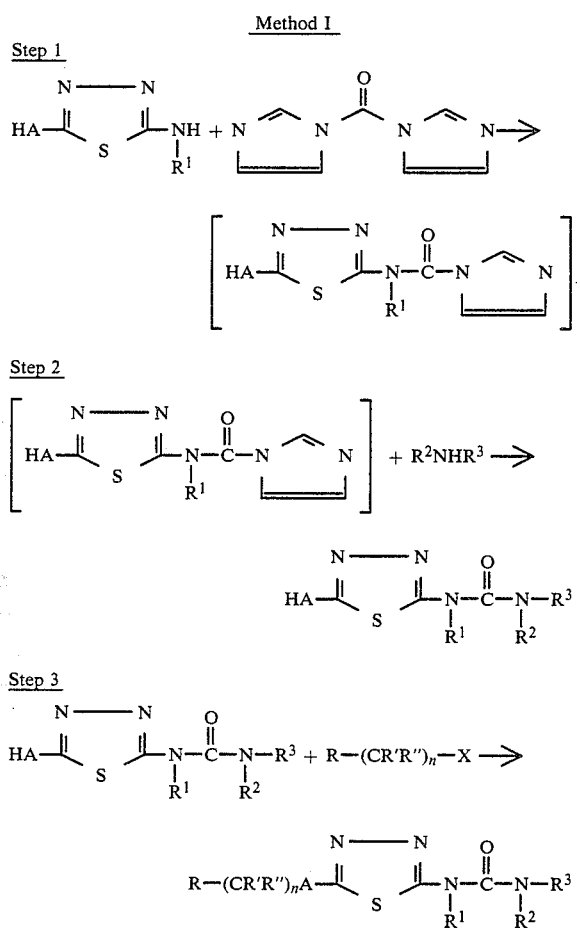

Method I

In step 1, the thiadiazole amine starting material above is first reacted with 1,1'-carbonyldiimidazole to form the bracketed urea intermediate. When R$^1$ is hydrogen, this urea intermediate will degrade into an isocyanate, which will in turn react with the amine in step 2 to form the desired thiadiazole urea intermediate. In step 2, the reaction product from step 1 i.e. the bracketed area intermediate or the isocyanate derived therefrom, is reacted with an amine having the formula R$^3$—NH—R$^2$ to form the desired thiadiazole urea intermediate. This intermediate is then reacted with an alkyl halide having the formula R—(CR'—R")$_n$—X, wherein X is chlorine, bromine or iodine, to produce the desired product. Each of these reactions is preferably conducted in an inert solvent such as ethyl acetate or toluene. This method is preferred over Method II, below, especially when R contains an active hydrogen atom due to its relative freedom from undesirable side reactions.

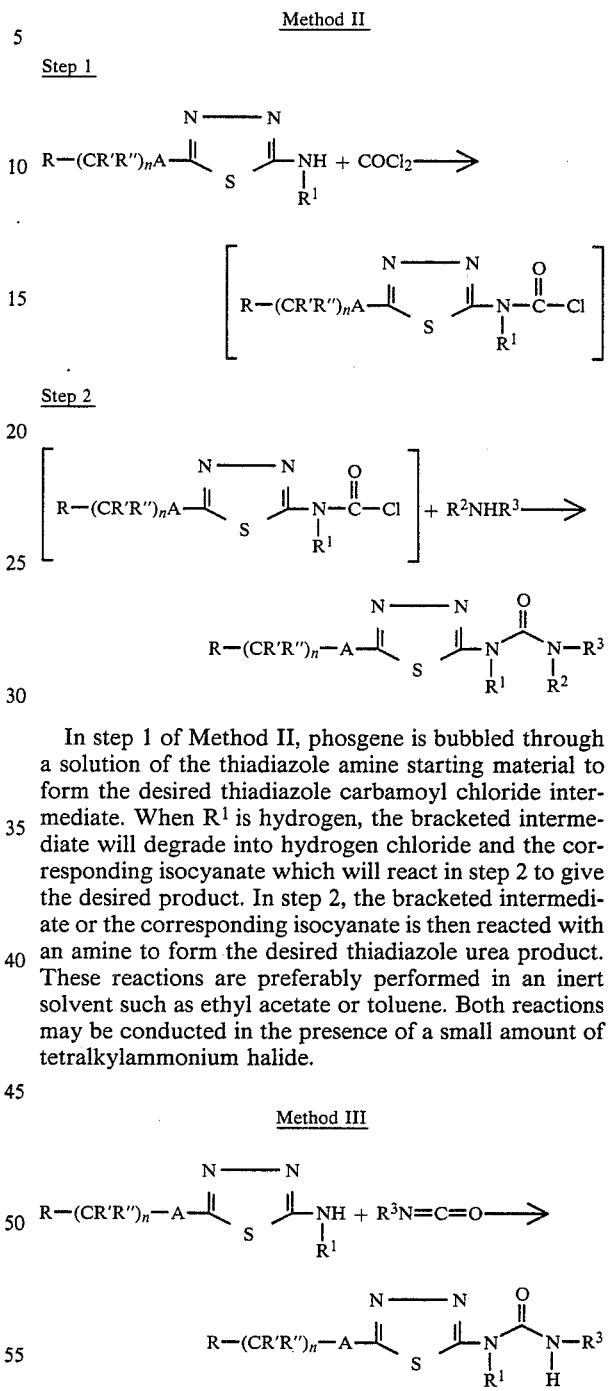

Method II

In step 1 of Method II, phosgene is bubbled through a solution of the thiadiazole amine starting material to form the desired thiadiazole carbamoyl chloride intermediate. When R$^1$ is hydrogen, the bracketed intermediate will degrade into hydrogen chloride and the corresponding isocyanate which will react in step 2 to give the desired product. In step 2, the bracketed intermediate or the corresponding isocyanate is then reacted with an amine to form the desired thiadiazole urea product. These reactions are preferably performed in an inert solvent such as ethyl acetate or toluene. Both reactions may be conducted in the presence of a small amount of tetralkylammonium halide.

Method III

Method III is particularly useful when R$^2$ is hydrogen. In this procedure, the appropriate thiadiazole amine starting material is reacted with an isocyanate to form the final urea product. The reaction is performed in an inert solvent such as ethyl acetate or toluene. The solvent should not contain water which can react with the isocyanate in an undesirable side reaction.

To prepare the compounds of this invention which have a cyclic urea moiety, a secondary amine reactant is selected that is capable of ring closure to form a cyclic urea after the initial formation of the acyclic urea. For example, the secondary amine reactant CH₃—N-H—CH₂—CH(OCH₃)₂, after acyclic urea formation, will cyclize in the presence of aqueous acid to form an imidazolidinoneurea. The intermediate acyclic urea need not be isolated before cyclization.

The preparation of the compounds of this invention wherein Y is sulfinyl or sulfonyl is simply effected by oxidizing the corresponding compound where Y is sulfur, with a suitable oxidizing agent such as sodium perborate. The procedures useful for such selective oxidations of sulfur compounds are disclosed in *Tetrahedron Letters*, vol. 24, p. 1505 (1983).

The thiadiazole amine reactant used in Method I can be prepared by methods known to those skilled in the art. For example, U.S. Pat. No. 4,252,962 discloses the mercapto-thiadiazole reactants used in Method I. The thiadiazole amine reactant used in the Method II and Method III can be made by the following general procedures.

The thiadiazole amine reactant can be prepared as follows:

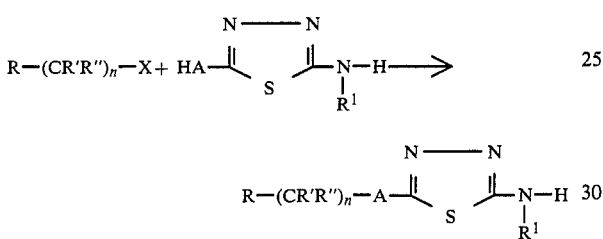

wherein, R, R', R" and R¹ are as previously defined, Y is sulfur and X is chlorine, or another reactive halogen. The reaction is preferably conducted in the presence of a base and a solvent. Suitable bases include sodium or potassium hydroxides, carbonates, ethoxides, or trialkylamines. Suitable solvents are lower alcohols, lower alkyl esters, lower ketones, lower sulfoxides, lower formamides, cyclic ethers, or halocarbons.

When n is 1, R¹ and R² are hydrogen, the alkyl halide reactant above can be prepared by reacting R—COOH with ethanol to form the ethyl ester R—COOCH₂CH₃, reacting the ethyl ester with sodium borohydride in ethanol to form the alcohol R—CH₂OH and reacting the alcohol with thionyl chloride to form the desired halogenated reactant R—CH₂—Cl.

When R is aryl or heteroaryl, such as thiophene, the halogenated reactant can be made by directly chloromethylating the appropriate aryl or heteroaryl starting material. For example, thiophene reacts with 40% aqueous formaldehyde in saturated aqueous hydrochloric acid to yield 2-chloromethylthiophene.

When Y is oxygen or alkylamine and R is phenyl, the thiadiazole amine reactant can be prepared as follows:

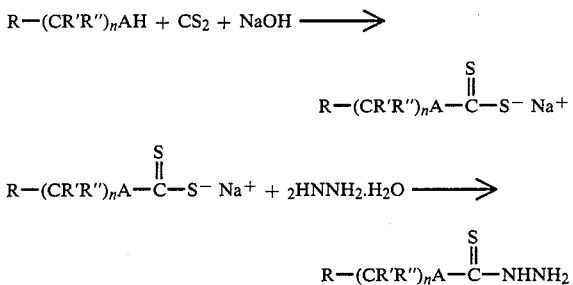

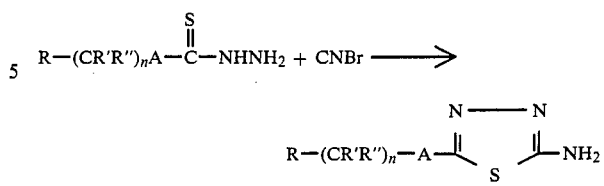

The alcohol or amine reactant is reacted with at least a stoichiometric amount of carbon disulfide in an aqueous alkali metal base to form the dithiocarbonate salt which, after isolation, is then reacted with aqueous hydrazine while cooling to about 5° C., to form the desired hydrazo-thiocarbamate intermediate. The hydrazo-thiocarbamate intermediate is then treated with a cyanogen halide in aqueous methanol to produce the thiadiazole amine intermediate. The resulting thiadiazole amine intermediate can be alkylated, if desired, before use in Method II.

EXAMPLES

The following examples more particularly illustrate the procedures described in the above methods of preparing the compounds of this invention.

EXAMPLE I

Preparation of
1,1,3-trimethyl-3-[5-(2-thienylmethylthio-1,3,4-thiadiazole-2-yl]urea (Method I)

1. 5-methylamino-2-[2-thienylmethylthio]-1,3,4-thiadizole

In a 100 ml three neck round bottom flask equipped with an addition funnel, magnetic stirrer, nitrogen atmosphere and an ice bath were mixed dichloromethane (30 ml) and thiophene-2-carbinol (5.2 g, 45.5 mmol). The addition funnel was charged with thionyl chloride (6.5 g, 54.0 mmol) diluted with dichloromethane (10 ml), and this solution was added slowly dropwise. When the addition was complete, the reaction mixture was stirred on an ice bath for 2 hours, was transferred to a separatory funnel and was washed with ice cold 10% aqueous sodium hydroxide (1×100 ml). The organic phase was separated and was immediately dried over MgSO₄. This solution was filtered by gravity into an addition funnel fitted to a 250 ml round bottom flask under a nitrogen atmosphere with a magnetic stirrer. In this flask were placed 5-methylamino-2-mercapto-1,3,4-thiadiazole (7.9 g, 54.0 mmol), dichloromethane (80 ml) and triethylamine (6.0 g, 60 mmol). The solution in the addition funnel was added relatively rapidly at room temperature, and the reaction was allowed to stand at room temperature overnight. The reaction mixture was washed with water (2×100 ml) and was dried over MgSO₄. The solvent was removed on a flash evaporator to leave a pale tan solid residue which was dried in vacuo, 9.3 g, 84.9% yield. mp 66.5°–67.5° C. IR: (KBr) 3170, 2960, 1575, 1550, 1510, 1435, 1400, 1230, 1140, 860, 840, 820, 780, 690, 640, 600 cm⁻¹ NMR: (CDCl₃) 7.0 (m, 4H), 4.5 (S, 2H), 2.95 (S, 3H)

2. 1,1,3-trimethyl-3-[5-(2-trienylmethylthio)-1,3,4-thiadiazol-2-yl]urea

In a 1 liter round bottom flask equipped with a heating mantle, nitrogen atmosphere and mechanical stirrer were mixed dichloromethane (250 ml) and 1,1'-carbonyldiimidazole (21.9 g, 0.135 mol). To this was added at room temperature, a solution of 5-methyl-amino-2-[2-thienylmethylthio]-1,3,4-thiadiazole (30.0 g, 0.123 mol) in 250 ml of ethyl acetate/dichloromethane (1:1.5). The mixture was heated to reflux for 3 hours. The reaction mixture was diluted with dichloromethane (300 ml) and was washed with water (3×200 ml) and the organic phase was dried over MgSO$_4$. The solvents were stripped to give a thick brown oil. 38.3 g, 99% yield. IR: (neat) 3010, 2960, 1650, 1480, 1470, 1420, 1360, 1310, 1250, 1165, 1110, 1040, 1015, 925, 875, 850, 835, 800, 750, 700, 640, 605 cm$^{-1}$ NMR: (CDCl$_3$) 6.75-7.30 (m, 3H), 4.65 (S, 2H), 3.5 (S, 3H), 2.95 (S, 6H). Analysis [Waters radial pack S-10 silica gel developed with 0.5% methanol in dichloromethane] one major peak, 94.7% pure.

EXAMPLE II

Preparation of
1,1,3-trimethyl-3-[5-(3-methylisoxazol-5-ylmethylthio)-1,3,4-thiadiazol-2-yl]urea (Method I)

1. 1,1,3-trimethyl-3-[5-mercapto-1,3,4-thia diazol-2-yl]urea

In a 1000 ml Round bottom flask equipped with a mechanical stirrer, heating mantle and an additional funnel under a nitrogen atmosphere were mixed ethyl acetate (400 ml), 1,1-carbonyldiimidazole (123.2 g, 0.74 mol) and 5-methylamino-2-mercapto-1,3,4-thiadizole. The mixture was heated to reflux for four hours. A dry ice cooled condenser was fitted to the flask and a solution of anhydrous dimethylamine (50.0 g, 1.1 mol) in ethyl acetate was added dropwise over a period of 30 minutes and the mixture was refluxed several hours. The reaction mixture was extracted with water (1×400 ml and 1×250 ml) and the organic phase was set aside. The aqueous solution was made acidic by the addition of ice and glacial acetic acid. A white solid precipitate was collected by suction filtration, was rinsed well with water and was then dried in vacuo over CaSO$_4$, 132.4 g, 81.9% yield; NMR: (DMSO-d$_6$) 7.0 (broad S, 1H), 3.1 (S, 3H), 2.8 (S, 6H) mp 190°-194° C. dec.

2. 1,1,3-trimethyl-3-[5-(3-methylisoxazol-5-yl-methylthio)-1,3,4-thiadiazol-2-yl]urea In a 100 ml round bottom flask were mixed 3-methyl-5-chloromethylisoxazole (1.5 g, 11 mmol), tetrahydrofuran (50 ml), 1,1,3-trimethyl-3-(5-mercapto-1,3,4-thiadiazol-2-yl) urea (2.5 g, 11 mmol) and triethylamine (5.1 g, 50 mmol). This was stirred at room temperature overnight. The reaction mixture was filtered and the solvent was stripped from the filtrate on a rotary evaporator. The residue was dissolved in dichloromethane and this was washed with water (2×60 ml) and the organic solution was dried over MgSO$_4$. This was treated with decolorizing carbon, was filtered and the solvent was removed to give a pale tan oil which was dried in vacuo, 2.9 g, 84.1% yield. NMR: (CDCl$_3$) 6.2 (S, 1H), 4.5 (S, 2H), 3.55 (S, 3H), 2.95 (S, 6H), 2.25 (S, 3H). IR (neat) 3120, 2960, 2930, 1660, 1600, 1480, 1440, 1410, 1370 1305, 1265, 1125, 1080, 1060 cm$^{-1}$. Calcd: C, 42.16; H, 4.82; N, 22.35. Found: C, 42.06; H, 4.90; N, 22.10.

EXAMPLE III

Preparation of 1,1,3-trimethyl-3-[5-(2-2-trimethyl etherthio)-1,3,4-triadiazol-2-yl]urea (Method I)

In a 250 ml round bottom flask were mixed 2-(2-chloroethyl) thiophene (3.0 g, 0.02 mol), 1,1,3-trimethyl-3-(5-mercapto-1,3,4-thiadiazol-2-yl) urea (4.4 g, 0.02 mol), potassium carbonate (5.5 g, 0.04 mol) and 2-butanone (80 ml). This was heated to reflux overnight and was then filtered and the filtrate was stripped of solvent. The residue was purified by flash chromatography on silica gel to give a thick almost colorless oil, 4.0 g, 60.9% yield. IR (neat) 2950, 1650, 1500, 1449, 1400, 1380, 1300, 1280, 1240, 1110, 1060, 700 cm$^{-1}$.

NMR: (CDCl$_3$) 7.0 (m, 3H), 3.5 (S, 3H), 3.3 (t, 4H), 3.0 (S, 6H). Calcd: C, 43.88; H, 4.91; N, 17.06. Found: C, 43.63; H, 4.83; N,17.12.

EXAMPLE IV

Preparation of
1-methyl-4-hydroxy-3-[5-(2-thienyl-methylthio)-1,3,4-thiadiazol-2-yl]imidazolin-2-one 1. 1-methyl-1-(2,2-dimethyoxyethyl)-3-(5-mercapto-1,3,4-thiadiazol-2-yl)urea (Method I)

In a 3 neck round bottom flask equipped with a mechanical stirrer, reflux condenser, heating mantle, addition funnel and nitrogen atmosphere were mixed ethyl acetate (80 ml), 1,1'-carbonyldiimidazole (25 g, 0.15 mol), and 5-mercapto-2-amino-1,3,4-thiadiazole (20.0 g, 0.15 mol). The mixture was stirred under reflux for three hours, was cooled and then a solution of methylamino acetaldehyde dimethylacetal (19.1 g, 0.16 mol) in ethyl acetate (30 ml) was added dropwise. Reflux was reinitiated and maintained for one hour. The cooled reaction mixture was extracted with water (2×100 ml) and the aqueous phase was made acidic by the addition of ice and glacial acetic acid. An oil separated which was extracted into ethyl acetate. The solvent was stripped to give a solid, 35.7 g, 85.5% yield, mp 92°-96° C.

IR(RBr): 3100, 2900, 1725, 1659, 1550, 1500, 1400, 1310, 1290, 1250, 1200, 1155, 1125, 1060, 800, 700.

NMR (CDCl$_3$ plus DMSO-d$_6$) 7.5 (S, 2H), 4.5 (t, 1H), 3.3 (S, 6H), 3.0 (S, 3H), 2.0 (S, 1H).

2. 1-methyl-4-hydroxy-3-[5-mercapto-1,3,4-thiadiazol-2-yl]imidazolin-2-one

In a 500 ml round bottom flask were mixed 1-methyl-1-(2,2-dimethoxyethyl)-3-(5-mercapto-1,3,4-thiadiazol-2-yl) urea (8.0 g, 0.03 mol), water (300 ml) and conc. hydrochloric acid (4 ml). The mixture was stirred vigorously and was heated to reflux for ~1 hour. The mixture was cooled and filtered to give a white solid product which was dried in vacuo, 5.3 g, 76.1% yield, mp 243° C. dec. NMR (NaOD in D$_2$O) 6.0 (t, 1H), 3.5 (d, 2H), 3.0 (S, 3H). IR: (KBr) 3400, 3200, 2900, 1700, 1550, 1500, 1450, 1360, 1275, 1245, 1100, 1080, 1050, 1000, 900, 775, 725.

3. 1-methyl-4-hydroxy-3-[5-(2-thienylmethyl-thio)-1,3,4-thiadiazol-2-yl]imidazolin-2-one In a round bottom flask equipped with a magnetic stirrer, ice bath, addition funnel and nitrogen atmosphere were mixed 2-thiophene carbinol (6.0 g, 0.05 mol), dichloromethane (100 ml) and triethyl amine (6.6 g, 0.065 mol). The reaction was cooled to 0° C. and thionyl chloride (7.14 g, 0.06 mol) diluted with dichloromethane (10 ml) was added dropwise at a rate such that the temperature remained below 10° C. The reaction was then allowed to warm to room temperature, was mixed in a large beaker with water (120 ml) and was neutralized by the addition of solid sodium bicarbonate to pH=7. The layers were separated; the organic layer was dried over MgSO$_4$ and was immediately filtered into an addition funnel fitted to a round bottom flask charged with dichloromethane (100 ml), 1-methyl-4-hydroxy-3-[5-mercapto-1,3,4-thiadiazol-2-yl]urea (12.8 g, 0.055 mol) and triethylamine (6.6 g, 0.065 mol). The solution was added relatively quickly at room temperature and after 1 hour, water (150 ml) was added to the reaction; the layers were separated, and the organic layer was washed again with water (1×250 ml) and was dried over MgSO$_4$. The solvents were stripped on a rotary evaporator to leave a solid, 13.2 g, 80.4% yield. This was recrystallized by the cloud point method using ethylacetate and hexane to give pure product, mp 129°-132° C. IR: (KBr) 1700, 1500, 1430, 1400, 1390, 1360, 1340, 1300, 1280, 1210, 1100, 1010, 900, 700.

NMR: (CDCl$_3$ plus DMSO-d$_6$) 7.0 (m, 4H), 6.0 (S, 1H), 4.6 (S, 2H), 3.5 (m, H), 3.3 (d, 1H), 2.9 (S, 3H). Calcd: C, 40.23; H, 3.68; N, 17.06. Found: C, 40.29; H, 3.83; N, 16.83.

EXAMPLE V

Preparation of 1,3-dimethyl-3-[-5-(6-chloropyrid-2-yl)methylthio-1,3,4-thiadiazole-2-yl]urea (Method III)

1. Preparation of 6-chloro-2-picoline-N-oxide.

6-Chloro-2-picoline (50 g, 0.39 mol) and glacial acetic acid (500 ml) were mixed in a one liter round-bottom flask and the mixture was warmed on a steam bath. To this mixture, 76 ml (0.66 mole) of 30% aqueous hydrogen peroxide was slowly added dropwise, heating for three hours on the steam bath after the addition was complete. The flask was fitted with a short path vacuum distillation head and about 150 ml of liquid were distilled from the reaction mixture. Water (100 ml) was added to the reaction and another 100 ml of distillate were collected. This was repeated until the reaction mixture gave a negative test for peroxide with starch/iodide paper. The reaction mixture was stripped under reduced pressure to give a brown oil which was then subjected to a high vacuum (about 0.2 torr) for several hours at 60° C. (oil bath) to remove the remaining acetic acid and water. This material (47.9 g, 85% yield) was carried on the next step without further purification.

2. Preparation of 2-chloromethyl-6-chloropyridine.

A 1/lt. three-neck round-bottom flask was equipped with mechanical stirrer, reflux condenser and two addition funnels. In the flask were placed 45.0 g. (0.32 mol) of 6-chloro-2-picoline-N-oxide and 100 ml of methylene chloride. In one addition funnel was placed a solution of triethylamine (36.0 g, 0.36 mol) diluted to 60 ml with CH$_2$Cl$_2$ and in the other was placed phosphorous oxychloride (54.6, 0.36 mol) diluted to 60 ml with CH$_2$Cl$_2$. With stirring, about 6 ml of the POCl$_3$ solution was added and then both addition funnels were adjusted to slowly drip in the respective solutions at the same rate. An exothermic reaction was observed. After the addition was complete, the mixture was stirred for two hours, poured on ice (200 ml) and the layers were separated. The organic solution was treated with decolorizing carbon, dried over MgSO$_4$ and was stripped, to give a dark colored semisolid. A portion of this semisolid was sublimed at 40° C. and 0.25 torr to give colorless crystals. Total yield about 60%. NMR: (CDCl$_3$) 7.8–7.1 (m,3H), 4.6 (s,2H).

3. Preparation of 5-methylamino-2-(6-chloropyrid-2-yl)methylthio-1,3,4-thiadiazole.

In a 250 ml round-bottom flask equipped with a mechanical stirrer were mixed 5-methylamino-2-mercapto-1,3,4-thiadiazole (5.4 g, 0.04 mol), dimethyl formamide (80 ml) and anhydrous potassium carbonate (6.1 g, 0.04 mol). The mixture was warmed to 35° C. and a solution of 6-chloro-2-chloromethylpyridine (6.0 g, 0.04 mol) in DMF (20 ml) was added dropwise. The reaction mixture was maintained at 40° C. for 2 hours after the addition was complete. The reaction mixture was filtered and stripped nearly to dryness. A solid was isolated by filtration and was dried in vacuo, 4.2 g, 41.6% yield, with a m.p. of 114°–115.5° C. NMR: (CDCl$_3$/DMSO-d$_6$) 8.9–7.1 (m,4H), 4.3 (s,2H), 3.2 (s,1H), 2.9 (s,3H). IR: (KBr) 3450, 3200, 1540, 1580, 1180, 1120, 980 cm$^{-1}$ 4. Synthesis of 1,3-dimethyl-3-[5-(6-chloropyrid-2-yl)methylthio-1,3,4-thiadiazol-2-yl]urea. In a 250 ml round-bottom flask were mixed 5-methylamino-2-(6-chloro-2-pyridyl)methylthio-1,3,4-thiadiazole (4.1 g, 0.015 mol), ethyl acetate (100 ml) and methyl isocyanate (5 ml). This mixture was heated to reflux for 1.5 hours, was cooled on an ice bath and was filtered by suction to give a white amorphous solid (3.7 g, 74.8%) with a m.p. of 153°–155.5° C. NMR: (CDCl$_3$/DMSO-d$_6$) 7.8–7.1 (m,4H), 4.5 (s,2H), 3.5 (s,3H), 2.7 (d,3H).

IR: (KBr) 3300, 1660, 1220, 880. Calc'd: C, 40.05; H, 3.66 N, 21.23; Found: C, 40.20; H, 3.81; N, 20.99.

EXAMPLE VI

Preparation of 1,3-dimethyl-3-[5-(6-chloropyrid-3-yl)methylthio-1,3,4-thiadiazol-2-yl]urea (Method III)

1. Preparation of ethyl-6-chloronicitoate.

In a 1 liter flask were mixed ethanol (200 ml) and 6-chloronicotinic acid (100 g, 0.63 mol). Sulfuric acid (200 ml) was added slowly dropwise, allowing the reaction to warm to about 70° C. Heating at 65°–70° C. was continued for 2 hours. The reaction mixture was poured on 2 liters of ice water. A precipitate was isolated and dried in vacuo, to yield 104.7 g, 89% yield, with a m.p. of 30° C. NMR: (CDCl$_3$) 8.95 (d,7H), 8.2 (q,1H), 7.3 (d,1H), 4.35 (q,2H), 1.4 (t,3H). IR: (neat) 2995, 1135.

2. Preparation of 6-chloro-3-pyridyl-methanol.

In a 4 liter beaker were mixed absolute ethanol (1 liter) and sodium borohydride (12.5 g, 0.33 mol) and the mixture was stirred and cooled with an ice bath. A solution of ethyl 6-chloronicitinoate (15.1 g, 0.08 mol) in ethanol (100 ml) was added slowly dropwise. The temperature of the reaction rose to 10°–15° C. during the addition and was allowed to rise slowly to room temperature when addition was complete. The yellow mixture was heated to 45°–50° C. until the color disappeared, about 2–4 hours. Ice water (600 ml) was added and the mixture was extracted with ether (2×300 ml). The organic extracts were washed with brine, dried over MgSO$_4$ and the solvents were stripped to give a viscous colorless oil of 10.7 g, 92% yield. NMR: (CDCl$_3$) 8.25–7.1 (m,3H), 4.7 (s,2H). IR: (neat) 3330, 2930, 1610, 1235 cm$^{-1}$ 3. Preparation of 6-chloro-3-chloromethylpyridine.

In a 250 ml round bottom flask were mixed 6-chloro-3-pyridylmethanol (10.0 g, 0.07 mol) and chloroform (100 ml). To this was added thionyl chloride (20.3 ml, 0.97 mol) and the mixture was warmed to reflux for one hour. The solvents were stripped to give a pale yellow solid of 8.4 g, 74.5% yield, with a m.p. of 29°–36° C. NMR: (CDCl$_3$) 8.18 (d,1H), 7.53 (d,1H), 7.15 (d,1H), 4.40 (s,2H);

IR: (KBr) 1573, 1130, 649 cm$^{-1}$.

4. Preparation of 5-methylamino-2-(6-chloropyrid-3-yl)methylthio-1,3,4-thiadiazole.

In a 1 liter round bottom flask were mixed potassium carbonate (36.7 g, 0.27 mole) and dimethylformamide (DMF) (300 ml), 5-methylamino-2-mercapto-1,3,4-thiadiazole (37.3 g, 0.25 mol). The solution was warmed to 40° C. and a solution of 6-chloro-3-chloromethylpyridine (41.0 g, 0.25 mol) in DMF (75 ml) was slowly added dropwise. When addition was complete, heating at 45°–50° C. was continued for 2 hours. The reaction mixture was filtered and stripped to a thick oil. The residue was poured on 1 liter ice water and a tan precipitate formed which was isolated by suction filtration and was dried in vacuo to yield 51.1 g, 74% yield, with a m.p. of 108°–111° C. NMR: (CDCl$_3$) 8.3 (d,1H), 7.5–7.8 (q,1H), 7.2 (t,1H), 6.4 (s,1H), 4.3 (s,2H), 3.0 (s,3H). IR: 3240, 1765, 660 cm$^{-1}$.

5. Synthesis of 1,3-dimethyl-3-[5-(6-chloropyrid-3-yl)methylthio-1,3,4-thiadiazol-2-yl]urea.

Procedure was identical to that shown in Example V, Part 4. The product was obtained in 74% yield with a m.p. of 177.5°–178.5° C. NMR: (DMSO-d$_6$) 8.3 (q,1H), 7.9 (q,1H), 7.4 (d,1H), 4.5 (s,2H), 3.6 (s, 3H), 2.8 (s,2H). Elemental analysis Calc'd for C$_{11}$H$_{12}$ClN$_5$OS$_2$: C, 40.06; H, 3.67; N, 21.23; Found C, 39.80; H, 3.67; N, 21.02.

EXAMPLE VII

Preparation of 1-methyl-3-[5-(phenylmethoxy)-1,3,4-thiadiazol-2-yl]urea (Method III)

1. Preparation of Benzyl alcohol xanthate potassium salt.

In a 500 ml round bottom flask were mixed toluene (200 ml), benzyl alcohol (50.5 g, 0.46 mole) and freshly powdered 85% KOH (33.0 g, 0.50 mole). While the mixture was stirred vigorously and cooled with an ice bath, carbon disulfide (60 ml, 1.0 mole) was added slowly dropwise at a rate such that the reaction was kept below 15° C. When the addition was complete, the yellow solid product was isolated by suction filtration and dried in vacuo to give 115 gms of solid in quantitative yield, m.p. 200° C. dec.

2. Preparation of (Benzyloxythiocarbonyl)hydrazine.

In a small flask equipped with a mechanical stirrer were mixed benzyl alcohol xanthate potassium salt (55.6 g, 0.25 mole) and water (50 ml). The solution was cooled to 10°–15° C. and hydrazine hydrate (15 ml) was slowly added dropwise. When the addition was complete, the reaction was allowed to warm to room temperature and the pH was adjusted to PH=7 by addition of acetic acid. Yellow plate-like crystals separated and were isolated by suction filtration, to yield 28.6 g, 63% yield. IR: (KBr) 3260, 1485, 1095, 1050, 693 cm$^{-1}$.

3. Preparation of 5-amino-2-benzyloxy-1,3,4-thiadiazole

In a 250 ml round-bottom flask equipped with a mechanical stirrer were mixed (benzyloxythiocarbonyl)hydrazine and 2N sodium hydroxide (90 ml). This mixture was stirred vigorously and cooled to 0° C. A solution of cyanogen bromide (14.5 g, 0.137 mol) in methanol (60 ml) was added dropwise at a rate that kept the reaction temperature between about 0°–5° C. A precipitate formed. When the addition was complete, the reaction mixture was filtered and the residue was rinsed well with water and dried in vacuo. The product was recrystallized from methanol/water to give a white solid of 16.6 g, 58.5% yield with a m.p. of 173°–175° C.

4. Synthesis of 1-methyl-3-[5-(phenyl methoxy)-1,3,4-thiadiazol-2-yl]urea.

In a 250 ml round-bottom flask were mixed 5-amino-2-benzyloxy-1,3,4-thiadiazole (3.0 g, 0.014 mol), ethyl acetate (100 ml) and methyl isocyanate (2.0 ml, 0.03 mol). This mixture was heated to reflux for 3 hours, was allowed to cool and was filtered. The solvents were stripped to give an oil of 1.0 g, 27% yield. IR: (neat) 3300, 1695, 1505, 1260, 1240, 698 cm$^{-1}$.

EXAMPLE VIII

Preparation of 1,3-dimethyl-3-[5-(5-chlorothiophen-2-yl)methylthio-1,3,4-thiadiazol-2-yl]urea (Method III)

1. Preparation of 5-chloro-2-chloromethyl thiophene

In a 250 ml round-bottom flask equipped with a mechanical stirrer and an ice/salt bath, were mixed concentrated aqueous hydrochloric acid (40 ml) and 2-chlorothiophene (40 g, 0.34 mol). This mixture was cooled to 0° C. and a stream of gaseous HCl was introduced under the surface of the mixture. A 40% aqueous solution formaldehyde (40 ml) was added dropwise, and the temperature was maintained at 3°–8° C. When the addition was complete, stirring was continued for 20 minutes, while HCl gas was continuously passed through the reaction mixture. The resulting mixture was poured on 120 ml ice/water. An oil was separated and the aqueous solution was extracted with ether (2×100 ml). The combined organic extracts were washed with water (2×100 ml) and were dried over anhydrous potassium carbonate. The solvents were stripped and the residue was distilled in vacuo, to collect 33.1 g, 58.6% yield, of a colorless liquid, with a b.p. of 50°–53° C. at 0.35 torr. NMR: (CDCl$_3$) 6.7 (m,2H), 4.6 (s,2H).

2. Preparation of 5-methylamino-2-(5-chlorothiophen-2-yl)-1,3,4-thiadiazole.

In a 250 ml round-bottom flask equipped with a mechanical stirrer, were mixed 5-chloro-2-chloromethylthiophene (10.0 g, 0.06 mol), 5-methylamino-2-mercapto-1,3,4-thiadiazole (8.7 g, 0.06 mol) tetrabutylammonium bromide (1.0 g) and acetone (100 ml). The mixture was stirred at room temperature overnight and was filtered. The residue was stirred with water (150 ml) for 1 hour, filtered, and dried in vacuo, to yield 6.3 g, 37.2% yield. NMR: (DMSO-d$_6$) 6.9 (s,2H), 4.55 (s,2H), 3.3 (s,3H), 2.85 (m,3H), m.p. 122°–124° C.

3. Preparation of 1,3-dimethyl-3-[5-(5-chlorothiophen-2-yl)methylthio-1,3,4-thiadiazol-2-yl]urea.

This compound was prepared as in accordance with the procedure of Example V, Part 4.

NMR: (DMSO-d$_6$) 6.9 (s,2H), 7.6 (s,1H), 4.65 (s,2H), 3.55 (s,3H), 2.75 (m,3H). Calc'd for C$_{10}$H$_{11}$ClN$_4$OS$_3$: C, 35.87; H, 3.31; N, 16.73 Found: C, 35.15 H, 3.23; N, 15.93, m.p. 52°–60° C.

The following compounds are illustrative of the novel compounds of this invention and can be prepared by the methods described above:

1,1,3-trimethyl-3-[5-(-1-(N-methylpyrrol-2-yl)-ethylthio)-1,3,4-thiadiazol-2-yl]urea;
1,1,3-trimethyl-3-[5-(2-(furan-3-yl)isopropylthio)-1,3,4-thiadiazol-2-yl]urea;
1,1,3-trimethyl-3-[5-(1-(thien-3-yl)ethylthio)-1,3,4-thiadiazol-2-yl]urea;
1,3-dimethyl-1-methoxy-3-[5-(2-tetrahydrofuranyl)-methylthio-1,3,4-thiadiazol-2-yl]urea;
1,3-dimethyl-3-[5-(indol-2-yl)methylthio-1,3,4-thiadiazole-2-yl]urea;
1,3-dimethyl-1-methoxy-3-[5-(isoindol-3-yl)methylthio-1,3,4 thiadiazol-2-yl]urea;
1,1,3-trimethyl-3-[5-(benzofuran-2-yl)methylthio-1,3,4-thiadiazol-2-yl]urea;
1,3-dimethyl-3-[5-(1-benzo[b]thien-3-yl)ethylthio)-1,3,4-thiadiazol-2-yl]urea;
1,1,3-trimethyl-3-[5-(1-(isobenzofuran-1-yl)ethylthio)-1,3,4-triadiazol-2-yl]urea;
1,3-dimethyl-3-methoxy-3-[5-(1-(benzo[c]thien-1-yl)ethylthio)-1,3,4-thiadiazol-2-yl]urea;
1,1,3-trimethyl-3-[5-(2-(6-trifluoromethylpyridin-2-yl)isopropylthio)-1,3,4-thiadiazol-2-yl]urea;
1,1,3-trimethyl-3-[5-(4H-pyran-2-yl)methylthio-1,3,4-thiadiazol-2-yl]urea;
1,1,3-trimethyl-3-[5-(quinol-3-yl)methylthio-1,3,4-thiadiazol-2-yl]urea;
1,3-dimethyl-1-ethyl-3-[5-(isoquinol-3-yl)methylthio-1,3,4-thiadiazol-2-yl]urea;
1,3-dimethyl-1-methoxy-3-[5-(pyrazol-3-yl)methylthio-1,3,4 thiadiazol-2-yl]urea;
1,3-dimethyl-3-[5-(1-(imidazol-2-yl)ethylthio)-1,3,4-thiadiazol-2-yl]urea;
1,3-dimethyl-3-[5-(tetrahydroimidazol-2-yl)methylthio-1,3,4-thiadiazol-2-yl]urea;
1,1,3-trimethyl-3-[5-(isooxazol-3-yl)methylthio-1,3,4-thiadiazol-2-yl]urea;
1,1,3-trimethyl-3-[5-(1-(1,3-oxozol-2-yl)ethylthio)-1,3,4-thiadiazol-2-yl]urea;
1,3-dimethyl-1-methoxy-3-[5-(2-isothiazol-3-yl)isopropylthio)-1,3,4-thiazol-2-yl]urea;
1,3-dimethyl-1-ethyl-3-[5-(1-(2H-imidazol-3-yl)ethylthio)-1,3,4-thiadiazol-2-yl]urea;
1,3-dimethyl-1-cyclohexyl-3-[5-(1-(3H-dithiol-5-yl)n-propylthio)-1,3,4-thiadiazol-2-yl]urea;
1,3-dimethyl-3-[5-(2H-1,3-oxathiol-2-yl)methylthio-1,3,4-thiadiazol-2-yl]urea;
1,3-dimethyl-1-methoxy-3-[5-(3H-1,2-dioxol-4-yl)methylthio-1,3,4-thiadiazol-2-yl]urea;
1,1,3-trimethyl-3-[5-(1-(1,3-dioxolan-2-yl)ethylthio)-1,3,4-thiadiazol-2-yl]urea;
1,1,3-trimethyl-3-[5-(2-(pyridazin-3-yl)isopropylthio)-1,3,4-thiadiazol-2-yl]urea;
1,3-dimethyl-1-ethyl-3-[5-(1-pyrimidin-2-yl]urea;
1,3-dimethyl-3-[5-(pyrazin-2-yl)methylthio-1,3,4-thiadiazol-2-yl]urea;
1,1,3-trimethyl-3-[5-(1,2-oxazin-2-yl)methylthio-1,3,4-thiadiazol-2-yl]urea;
1,3-dimethyl-1-methoxy-3-[5-(1,3-oxazin-2-yl)methylthio-1,3,4-thiadiazol-2-yl]urea;
1,1,3-trimethyl-3-[5-(2-(1,4-oxazin-2-yl)isopropylthio-1,3,4-thiadiazol-2-yl]urea;
1,3-dimethyl-3-[5-(2-(1,2-dioxan-3-yl)isopropylthio)-1,3,4-thiadiazol-2-yl]urea;
1,3-dimethyl-3-[5-(1-(1,3-oxathian-2-yl)ethylthio)-1,3,4-thiadiazol-2-yl]urea;

1,3-dimethyl-1-methoxy-3-[5-(1-(1,4-dithian-2-yl)ethylthio)-1,3,4-thiadiazol-2-yl]urea;
1,3-dimethyl-1-cyclopropyl-3-[5-(1-(1,3-dithian-2-yl)ethylthio)-1,3,4-thiadiazol-2-yl]urea;
1,1,3-trimethyl-3-[5-(1-(purin-9-yl)ethylthio)-1,3,4-thiadiazol-2-yl]urea;
1,3-dimethyl-3-[5-(1-(1,3,5-triazin-2-yl)ethylthio)1,3,4-thiadizol-2-yl]urea;
1,3-dimethyl-3-[5-(1,2,3-benzo[b]triazol-1-yl)methylthio-1,3,4-thiadiazol-2-yl]urea;
1,3-dimethyl-3-[5-(1,2,3-oxadiazol-4-yl)methylthio-1,3,4-thiadizol-2-yl]urea;
1,3-dimethyl-3-[5-(1-(1,2,4-oxadizol-3-yl)ethylthio)-1,3,4-thiadiazol-2-yl]urea;
1,3-dimethyl-3-[5-(1-(5-methyl-1,3,4-furazan-2-yl)n-propylthio)-1,3,4-thiadiazol-2-yl]urea;
1,1,3-trimethyl-3-[5-(4-methyl-1,2,3-thiadiazol-5-yl)methylthio-1,3,4-thiadiazol-2-yl]urea;
1,3-dimethyl-1-methoxy-3-[5-(1,2,4-thiadizol-3-yl)methylthio-1,3,4-thiadiazol-2-yl]urea;
1,3-dimethyl-3-[5-(1-(5-chloro-1,3,4-thiadiazol-2-yl)ethylthio)-1,3,4-thiadiazol-2-yl]urea;
1,3-dimethyl-3-[5-(1-(6-chloro-1,3-benzo[b]oxazol-2-yl)ethylthio)-1,3,4-thiadiazol-2-yl]urea;
1,3-dimethyl-3-[5-(1-(7-chloro-1,3-thiazol-2-yl)isopropyl-thio)-1,3,4-thiadiazol-2-yl]urea;
1,1,3-trimethyl-3-[5-(benzo[b]pyrazin-2-yl9isopropylthio-1,3,4-thiadiazol-2-yl]urea;
1,3-dimethyl-3-[5-(phthalimid-N-yl)methylthio-1,3,4-thiadiazol-2-yl]urea;
1,3-dimethyl-1-methoxy-3-[5-(succinimid-N-yl)methylthio-1,3,4-thiadiazol-2-yl]urea;
1,1,3-trimethyl-3-[5-(-1-(N-methylpyrrol-2-yl)ethoxy)-1,3,4-thiadiazol-2-yl]urea;
1,1,3-trimethyl-3-[5-(2-(furan-3-yl)isopropoxy)-1,3,4-thiadiazol-2-yl]urea;
1,1,3-trimethyl-3-[5-(1-(thien-3-yl)ethoxy)-1,3,4-thiadiazol-2-yl]urea;
1,3-dimethyl-1-methoxy-3-[5-(2-tetrahydrofuranyl)methoxy-1,3,4-thiadizol-2-yl]urea;
1,3-dimethyl-3-[5-(indol-2-yl)methoxy-1,3,4-thiadiazole-2-yl]urea;
1,3-dimethyl-1-methoxy-3-[5-(isoindol-3-yl)methylthio-1,3,4 thiadiazol-2-yl]urea;
1,1,3-trimethyl-3-[5-(benzofuran-2-yl)methoxy-1,3,4-thiadiazol-2-yl]urea;
1,3-dimethyl-3-[5-(1-benzo[b]thien-3-yl)ethoxy)-1,3,4-thiadiazol-2-yl]urea;
1,1,3-trimethyl-3-[5-(1-(isobenzofuran-1-yl)ethoxy)-1,3,4-triadiazol-2-yl]urea;
1,3-dimethyl-3-methoxy-3-[5-(1-benzo[c]thien-1-yl)ethoxy)-1,3,4-thiadiazol-2-yl]urea;
1,1,3-trimethyl-3-[5-(2-(6-trifluoromethylpyridin-2-yl)isopropoxy)-1,3,4-thiadiazol-2-yl]urea;
1,1,3-trimethyl-3-[5-(4H-pyran-2-yl)methoxy-1,3,4-thiadiazol-2-yl]urea;
1,1,3-trimethyl-3-[5-(quinol-3-yl)methoxy-1,3,4-thiadiazol-2-yl]urea;
1,3-dimethyl-1-ethyl-3-[5-(isoquinol-3-yl)methoxy-1,3,4-thiadiazol-2-yl]urea;
1,3-dimethyl-1-methoxy-3-[5-(pyrazol-3-yl)methoxy-1,3,4 thiadiazol-2-yl]urea;
1,3-dimethyl-3-[5-(1-imidazol-2-yl)ethoxy)-1,3,4-thiadiazol-2-yl]urea;
1,3-dimethyl-3-[5-(tetrahydroimidazol-2-yl)methylthio-1,3,4-thiadiazol-2-yl]urea;
1,1,3-trimethyl-3-[5-(isooxazol-3-yl)methoxy-1,3,4-thiadiazol-2-yl]urea;

1,1,3-trimethyl-3-[5-(1-(1,3-oxozol-2-yl)ethoxy)-1,3,4-thiadiazol-2-yl]urea;
1,3-dimethyl-1-methoxy-3-[5-(2-isothiazol-3-yl)isopropoxy)-1,3,4-thiazol-2-yl]urea;
1,3-dimethyl-1-ethyl-3-[5-(1-(2H-imidazol-3-yl)ethoxy)-1,3,4-thiadiazol-2-yl]urea;
1,3-dimethyl-1-cyclohexyl-3-[5-(1-(3H-dithiol-5-yl)n-propoxy)-1,3,4-thiadiazol-2-yl]urea;
1,3-dimethyl-3-[5-(2H-1,3-oxathiol-2-yl)methoxy-1,3,4-thiadiazol-2-yl]urea;
1,3-dimethyl-1-methoxy-3-[5-(3H-1,2-dioxol-4-yl)methoxy-1,3,4-thiadiazol-2-yl]urea;
1,1,3-trimethyl-3-[5-(1-(1,3-dioxolan-2-yl)ethoxy)-1,3,4-thiadiazol-2-yl]urea;
1,1,3-trimethyl-3-[5-(2-pyridazin-3-yl)isopropoxy)-1,3,4-thiadiazol-2-yl]urea;
1,3-dimethyl-1-ethyl-3-[5-(1-pyrimidin-2-yl)ethoxy)-1,3,4-thiadiazol-2-yl]urea;
1,3-dimethyl-3-[5-(pyrazin-2-yl)methoxy-1,3,4-thiadiazol-2-yl]urea;
1,1,3-trimethyl-3-[5-(1,2-oxazin-2-yl)methoxy-1,3,4-thiadiazol-2-yl]urea;
1,3-dimethyl-1-methoxy-3-[5-(1,3-oxazin-2-yl)methoxy-1,3,4-thiadiazol-2-yl]urea;
1,1,3-trimethyl-3-[5-(2-(1,4-oxazin-2-yl)isopropoxy-1,3,4-thiadiazol-2-yl]urea;
1,3-dimethyl-3-[5-(2-(1,2-dioxan-3-yl)isopropoxy)-1,3,4-thiadiazol-2-yl]urea;
1,3-dimethyl-3-[5-(1-(1,3-oxathian-2-yl)ethoxy)-1,3,4-thiadiazol-2-yl]urea;
1,3-dimethyl-1-methoxy-3-[5-(1-(1,4-dithian-2-yl)ethoxy)-1,3,4-thiadiazol-2-yl]urea;
1,3-dimethyl-1-cyclopropyl-3-[5-(1-(1,3-dithian-2-yl)ethoxy)-1,3,4-thiadiazol-2-yl]urea;
1,1,3-trimethyl-3-[5-(1-(purin-9-yl)ethoxy)-1,3,4-thiadiazol-2-yl]urea;
1,3-dimethyl-3-[5-(1-(1,3,5-triazin-2-yl)ethoxy)-1,3,4-thiadizol-2-yl]urea;
1,3-dimethyl-3-[5-(1,2,3-benzo[b]triazol-1-yl)methoxy-1,3,4-thiadiazol-2-yl]urea;
1,3-dimethyl-3-[5-(1,2,3-oxadiazol-4-yl)methoxy-1,3,4-thiadiazol-2-yl]urea;

1,3-dimethyl-3-[5-(1,2,4-oxadizol-3-yl)ethoxy)-1,3,4-thiadiazol-2-yl]urea;
1,3-dimethyl-3-[5-(1-(5-methyl-1,3,4-furazan-2-yl)n-propoxy)-1,3,4-thiadiazol-2-yl]urea;
1,1,3-trimethyl-3-[5-(4-methyl-1,2,3-thiadiazol-5-yl)methoxy-1,3,4-thiadiazol-2-yl]urea;
1,3-dimethyl-1-methoxy-3-[5-(1,2,4-thiadizol-3-yl)methoxy-1,3,4-thiadiazol-2-yl]urea;
1,3-dimethyl-3-[5-(1-(5-chloro-1,3,4-thiadiazol-2-yl)ethoxy-1,3,4-thiadizol-2-yl]urea;
1,3-dimethyl-3-[5-(1-(6-chloro-1,3-benzo[b]oxazol-2-yl)ethoxy)-1,3,4-thiadiazol-2-yl]urea;
1,3-dimethyl-3-[5-(1-(7-chloro-1,3-thiazol-2-yl)isopropyl-thio)-1,3,4-thiadiazol-2-yl]urea;
1,1,3-trimethyl-3-[5-(benzo[b]pyrazin-2-yl)isopropoxy-1,3,4-thiadiazol-2-yl]urea;
1,3-dimethyl-3-[5-(phthalimid-N-yl)methoxy-1,3,4-thiadiazol-2-yl]urea;
1,3-dimethyl-1-methoxy-3-[5-(succinimid-N-yl)methoxy-1,3,4-thiadiazol-2-yl]urea;
1-[5-(6-chloropyrid-2-yl)methylthio-1,3,4-thiadiazol-2-yl]-2-hydroxy-4-methyl-imidazolinoneurea;
1-[5-(benzothiazo-2-yl)methylthio-1,3,4-thiadiazol-yl]-2-methoxy-4-n-propyl-imdazolinoneurea;
1,3-dimethyl-3-[5-([6-chloro pyrid-2-yl]methylmethylamino)-1,3,4-thiadiazol-2-yl]urea;
1,3-dimethyl-3-[5-(6-chloropyrid-2-yl)methylsulfinyl-1,3,4-thiadiazol-2-yl]urea;
1,3-dimethyl-1-ethyl-3-[5-(thiophen-2-yl)methylsulfonyl-1,3,4-thiadiazol-2-yl]urea;
1,1,3-trimethyl-3-[5-(2-thiophen-2-yl)ethylthio)-1,3,4-thiadiazol-2-yl]urea;
1,3-trimethyl-3-[5-(5-(6-chloropyrid-2-yl)n-pentylthio)-1,3,4-thiadiazol-2-yl]urea;
1,3-diemthyl-1-methoxy-3-[5-(3-benzothiazo-2-yl)n-butyloxy)-1,3,4-thiadiazol-2-yl]urea; and
1-[5-(3-thiophen-2-yl)n-octylthio)-1,3,4-thiadiazol-2-yl)]-2-hydroxy-4-methyl-imidazolinoneurea.

The following tables, Tables I-VII, set forth the structure and physical-chemical data for representative compounds of this invention.

TABLE I

Physical/Chemical Data for
Pyridinyl-Substituted Thiadiazole Ureas

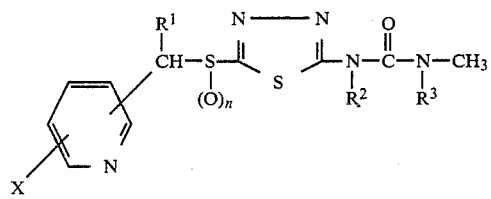

| Compound Number | Pyridinyl Position | X | $R^1$ | $R^2$ | $R^3$ | n | Melting Point (°C.) | Infra-red Spectrum (IR) or Elemental Analysis (EA) | | | | | |
|---|---|---|---|---|---|---|---|---|---|---|---|---|---|
| | | | | | | | | Calc. | | | Found | | |
| | | | | | | | | C | H | N | C | H | N |
| 1 | 2 | H | H | H | H | 0 | 165-170 (dec)[1] | IR(KBr): 3400, 3240(Br), 3180(Br), 2940, 2890(Br), 2780(Br), 1723, 1590, 1550(s), 1460, 1430, 1415, 1395, 1335, 1305, 1245, 1105, 1050, 995, 810, 780, 740, 680, 660, 605 cm$^{-1}$ | | | | | | |
| 2 | 2 | H | H | $CH_3$ | H | 0 | 151 (dec.) | IR(KBr): 3320(Br), 3060, 3000, 2940, 1665, 1595, 1580, 1560, 1530(Br), 1475(Br), 1430, 1400, 1320, 1300, 1210, 1150, 1100, 1050, 990, 890, 750, 630, 620 cm$^{-1}$ | | | | | | |
| 3 | 2 | H | H | $CH_3$ | $CH_3$ | 0 | oil | IR(neat): 3250(Br), 3000, 2930(Br), 1700, 1645(Br), 1490(Br), 1405, 1375, 1308, 1260(Br), 1135, 1060, 1045, 990, 910, 780, 745, 640 cm$^{-1}$ | | | | | | |
| 4 | 2 | H | $CH_3$ | $CH_3$ | H | 0 | oil | — | — | — | — | — | — |
| 5 | 2 | 6-Cl | H | $CH_3$ | H | 0 | 153-155.5 | EA: 40.05 | 3.66 | 21.23 | 40.20 | 3.81 | 20.99 |

TABLE I-continued

Physical/Chemical Data for
Pyridinyl-Substituted Thiadiazole Ureas $$R^1-\underset{X}{\underset{|}{\text{pyridinyl}}}-CH-S(O)_n-\underset{S}{\overset{N-N}{\diagdown\diagup}}-N(R^2)-\overset{O}{\overset{\|}{C}}-N(R^3)-CH_3$$

| Compound Number | Pyridinyl Position | X | $R^1$ | $R^2$ | $R^3$ | n | Melting Point (°C.) | Infra-red Spectrum (IR) or Elemental Analysis (EA) | | | | | |
|---|---|---|---|---|---|---|---|---|---|---|---|---|---|
| | | | | | | | | | Calc. | | | Found | |
| | | | | | | | | | C | H | N | C | H | N |
| 6 | 3 | H | H | H | H | 0 | oil | EA: | 42.58 | 3.96 | — | 45.26 | 4.17 | — |
| 7 | 3 | H | H | CH$_3$ | H | 0 | 121 (dec.) | IR(KBr): 32.75(Br), 3040, 2980, 2935, 1665, 1580, 1530, 1490(Br), 1455, 1420, 1410, 1340, 1290, 1210, 1150, 1100, 1063, 900, 800, 750, 710, 640, 630 cm$^{-1}$ | | | | | | |
| 8 | 3 | 2-Cl | H | H | H | 0 | oil | — | — | — | — | — | — | — |
| 9 | 3 | 2-Br | H | CH$_3$ | H | 0 | oil | — | — | — | — | — | — | — |
| 10 | 3 | 2-Cl | H | CH$_3$ | H | 0 | 168–169 | EA: | 40.06 | 3.67 | 21.23 | 40.06 | 3.70 | 21.35 |
| 11 | 3 | 2-Cl | H | CH$_3$ | CH$_3$ | 0 | 104–105.5 | EA: | 41.92 | 4.1 | 20.37 | 41.79 | 4.16 | 20.25 |
| 12 | 3 | 2-Cl | H | CH$_3$ | OCH$_3$ | 0 | 116.5–118 | EA: | 40.05 | 3.92 | 19.46 | 39.99 | 4.04 | 18.48 |
| 13 | 3 | 6-Cl | H | H | H | 0 | 216–218 | EA: | 38.03 | 3.19 | 22.18 | 38.96 | 3.27 | 21.66 |
| 14 | 3 | 6-Cl | H | CH$_3$ | H | 0 | 176.5–178 | EA: | 40.06 | 3.67 | 21.23 | 40.11 | 3.66 | 21.37 |
| 15 | 3 | 6-Cl | H | CH$_3$ | CH$_3$ | 0 | 75.5–78 | EA: | 41.92 | 4.10 | 20.37 | 42.00 | 4.14 | 20.30 |
| 16 | 3 | 6-Cl | H | H | CH$_3$ | 0 | 177.5–179 | EA: | 40.06 | 3.67 | 21.23 | 39.99 | 3.75 | 20.53 |
| 17 | 3 | 6-Cl | H | CH$_3$ | OCH$_3$ | 0 | 105–107.5 | EA: | 40.05 | 3.92 | 19.46 | 39.97 | 4.07 | 19.66 |
| 18 | 3 | 6-Cl | H | CH$_2$CH$_3$ | H | 0 | 144–146.5 | EA: | 41.19 | 4.10 | 20.36 | 41.98 | 4.13 | 20.29 |
| 19 | 3 | 6-Cl | H | CH$_3$ | p-Cl—phenyl | 0 | 168–169 | EA: | 40.06 | 3.67 | 21.23 | 40.06 | 3.70 | 21.35 |
| 20 | 3 | 6-Cl | H | CH$_3$ | H | 2 | 194.5–196 | EA: | 36.51 | 3.34 | 19.36 | 36.82 | 3.43 | 19.18 |
| 21 | 3 | 6-Cl | H | CH$_3$ | H | 1 | — | — | — | — | — | — | — | — |
| 22 | 3 | 6-Br | H | CH$_3$ | H | 0 | 179–182 | EA: | 35.30 | 3.23 | 18.71 | 36.64 | 3.29 | 18.76 |
| 23 | 3 | 6-CH$_3$ | H | CH$_3$ | H | 0 | 165–166 | EA: | 46.58 | 4.89 | 22.64 | 46.31 | 4.95 | 22.57 |
| 24 | 4 | H | H | H | H | 0 | 160–164 (dec.) | IR(KBr): 3390, 3250(Br), 3150(Br), 2940, 1690, 1680, 1605, 1530(Br), 1420(Br), 1290, 1240, 1230, 1140, 1069, 1020, 840, 810, 790, 750, 700, 675, Cm$^{-1}$ | | | | | | |
| 25 | 4 | H | H | CH$_3$ | H | 0 | 194–196 | IR(KBr): 3230, 3050, 2940, 1665(Br), 1600, 1550(Br), 1465(Br), 1400, 1310, 1210, 1140, 1090, 1050, 995, 890, 840, 815, 750, 690, 630 cm$^{-1}$ | | | | | | |

TABLE II

Physical/Chemical Data of
Benzyloxy-Substituted Thiadiazole Ureas $$R^1-CH_2-O-\overset{N-N}{\underset{S}{\diagdown\diagup}}-R^2$$

| Compound Number | $R^1$ | $R^2$ | Melting Point (°C.) | Infra-red Spectrum (IR) or Elemental Analysis (EA) | | | | | |
|---|---|---|---|---|---|---|---|---|---|
| | | | | | Calc. | | | Found | |
| | | | | | C | H | N | C | H | N |
| 26 | phenyl | N'—methylurea-N—yl | oil | IR(neat): 3300(Br), 2950, 1695, 1560(Br), 1505(Br), 1450, 1410, 1310, 1250(Br), 740(Br), 690, cm$^{-1}$ | | | | | |
| 27 | 2,6-dichlorophenyl | N'—methylurea-N—yl | 177–182 | EA: | 37.35 | 3.89 | 15.41 | 37.40 | 2.85 | 15.86 |
| 28 | 3-chlorophenyl | N'—methylurea-N—yl | 180–186 | EA: | 43.75 | 4.48 | 15.16 | 44.22 | 3.71 | 18.75 |
| 29 | 3-chlorophenyl | N'methyl-4-hydroxy-imidazolidoneurea-N—yl | oil | IR(neat): 3210(Br), 3080(Br), 2940, 1690(Br), 1580, 1470, 1430, 1370, 1260(Br), 1210, 1120, 1070, 940, 865, 810, 780, 650(Br) cm$^{-1}$ | | | | | |

TABLE III

Physical/Chemical Data for Thienyl-Substituted Thiadiazole Ureas

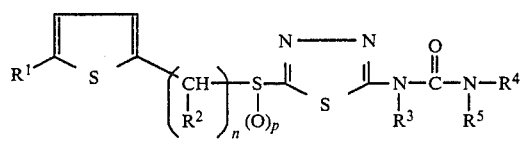

| Compound Number | Thienyl Position | n | P | R¹ | R² | R³ | R⁴ | R⁵ | Melting Point (°C.) | | Calc. C | Calc. H | Calc. N | Found C | Found H | Found N |
|---|---|---|---|---|---|---|---|---|---|---|---|---|---|---|---|---|
| 30 | 2 | 1 | 0 | H | H | CH₃ | CH₃ | H | 137.5–140 | EA: | 39.98 | 4.03 | 18.65 | 40.35 | 4.12 | 18.19 |
| 31 | 2 | 1 | 0 | Cl | H | CH₃ | CH₃ | H | 122–124 | EA: | 35.87 | 3.31 | 16.73 | 35.15 | 3.23 | 15.93 |
| 32 | 2 | 1 | 0 | Cl | H | CH₃ | CH₃ | CH₃ | oil | EA: | 37.87 | 3.75 | 16.06 | 37.88 | 3.92 | 16.23 |
| 33 | 2 | 1 | 0 | H | H | CH₃ | CH₃ | CH₃ | oil | IR(neat): | 3010, 2960, 1650, 1480, 1470, 1420, 1360, 1250, 1165, 1110, 1040, 1015, 925, 875, 850, 835, 800, 750, 700, 640, 605 Cm⁻¹ | | | | | |
| 34 | 2 | 1 | 0 | H | H | CH₃ | CH₃ | OCH₃ | oil | IR(neat): | 2940, 1640, 1460, 1410, 1380, 1310, 1275, 1240, 1130, 1060, 980, 850, 830, 770, 750, 700, 640 CM⁻¹ | | | | | |
| 35 | 2 | 1 | 0 | H | CH₃ | CH₃ | CH₃ | H | 93–99 | EA: | 62.02 | 4.49 | 17.82 | 40.40 | 18.65 | |
| 36 | 2 | 1 | 0 | H | CH₃ | CH₃ | CH₃ | CH₃ | oil | EA: | 43.88 | 4.91 | 17.06 | 42.07 | 4.92 | 18.12 |
| 37 | 2 | 2 | 0 | H | H | CH₃ | CH₃ | CH₃ | oil | EA: | 43.88 | 4.91 | 17.06 | 43.16 | 5.001 | 16.98 |
| 38 | 2 | 1 | 1 | H | H | CH₃ | CH₃ | H | 150–165 (dec) | EA: | 37.96 | 3.82 | 17.71 | 37.53 | 3.85 | 17.98 |
| 39 | 2 | 1 | 2 | H | H | CH₃ | CH₃ | H | 144–149.5 | EA: | 35.13 | 3.64 | 16.85 | 37.13 | 3.68 | 16.08 |
| 40 | 2 | 1 | 0 | CH₃ | H | CH₃ | CH₃ | H | 145–147.5 | EA: | 42.02 | 4.49 | 17.82 | 40.37 | 4.44 | 17.75 |
| 41 | 3 | 1 | 0 | H | H | CH₃ | CH₃ | H | 66.5–67.5 | EA: | 39.98 | 4.03 | 18.65 | 38.68 | 4.21 | 18.80 |
| 42 | 3 | 1 | 0 | H | CH₃ | CH₃ | CH₃ | CH₃ | oil | IR(neat): | 2950, 1735, 1490, 1400, 1780, 1300, 1125 cm⁻¹ | | | | | |
| 43 | 3 | 1 | 0 | H | CH₃ | CH₃ | CH₃ | H | 104.5–109 | EA: | 42.42 | 3.56 | 17.99 | 40.15 | 4.50 | 18.01 |
| 44 | 3 | 2 | 0 | H | H | CH₃ | CH₃ | CH₃ | oil | | — | — | — | — | — | — |

TABLE IV

Physical/Chemical Data for Thienyl-Substituted Cyclic Thialiazole Ureas

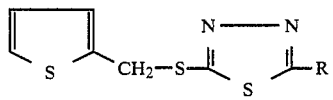

| Compound Number | R | Melting Point (°C.) | Calc. C | Calc. H | Calc. N | Found C | Found H | Found N |
|---|---|---|---|---|---|---|---|---|
| 45 | ![structure with N-C(O)-N-CH3, CH(OH)CH2] | 137–139 | 40.23 | 3.68 | 17.06 | 40.29 | 3.83 | 16.83 |
| 46 | ![structure with N-C(O)-N-CH3, CH(OCH3)CH2] | oil | 39.98 | 4.27 | 16.96 | 40.71 | 4.14 | 16.65 |
| 47 | ![structure with N-C(O)-N-CH3, CH=CH] | 97–97 | 42.56 | 3.26 | 18.05 | 41.02 | 3.86 | 15.56 |
| 48 | ![structure with N-C(O)-NH, O=C-NH] | 170.5–171.5 | 34.50 | 2.25 | 22.35 | 33.39 | 3.22 | 23.47 |

TABLE V

Physical/Chemical Data for
Isoxazole-Substituted Thiadiazole Ureas

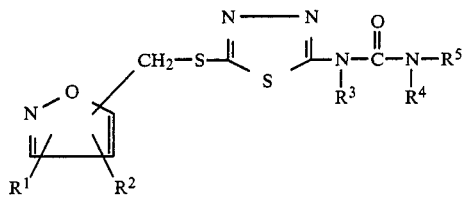

| Compound Number | Isoxazole Position | $R^1$ | $R^2$ | $R^3$ | $R^4$ | $R^5$ | Melting Point (°C.) | IR or EA | Calc. C | Calc. H | Calc. N | Found C | Found H | Found N |
|---|---|---|---|---|---|---|---|---|---|---|---|---|---|---|
| 49 | 5 | 3-CH₃ | H | CH₃ | CH₃ | H | oil | IR(KBr): 3300,2920,1660,1600,1535,1470,1400 1320,1210,1160,1100,1255,900,810,760, 600 cm⁻¹ | | | | | | |
| 50 | 4 | 3-CH₃ | 5-CH₃ | CH₃ | CH₃ | CH₃ | oil | EA: | 39.72 | 4.67 | 18.53 | 39.85 | 4.80 | 18.35 |
| 51 | 5 | 3(p-chlorophenyl) | H | CH₃ | CH₃ | CH₃ | 115–121 | EA: | 46.88 | 3.93 | 17.08 | 46.78 | 4.19 | 16.19 |
| 52 | 5 | 3-CH₃ | H | CH₃ | CH₃ | CH₃ | oil | EA: | 42.16 | 4.82 | 22.35 | 42.06 | 4.90 | 22.10 |
| 53 | 5 | 3(P-tolyl) | H | CH₃ | CH₃ | CH₃ | oil | EA: | 52.42 | 4.92 | 17.98 | 53.19 | 5.09 | 17.92 |

TABLE VI

Physical/Chemical Data for
Benzimidazol-Substituted Thiadiazole Ureas

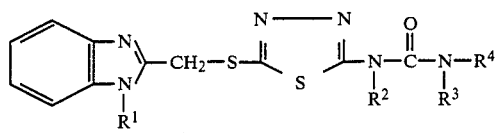

| Compound Number | $R^1$ | $R_2$ | $R_3$ | $R_4$ | Melting Point (°C.) | IR or EA | Calc. C | Calc. H | Calc. N | Found C | Found H | Found N |
|---|---|---|---|---|---|---|---|---|---|---|---|---|
| 54 | H | CH₃ | CH₃ | H | 188–190 | EA: | 46.69 | 4.22 | 25.13 | 47.75 | 4.91 | 22.49 |
| 55 | H | CH₃ | CH₃ | CH₃ | 112–116 | EA: | 48.82 | 4.63 | 24.12 | 46.06 | 5.03 | 22.85 |
| 56 | CH₃ | CH₃ | CH₃ | H | 169–172 | EA: | 48.82 | 4.63 24.12 | | 46.06 | 4.94 | 22.86 |
| 57 | CH₃ | CH₃ | CH₃ | CH₃ | 134–135.5 | EA: | 49.75 | 5.01 | 23.21 | 49.49 | 5.13 | 23.17 |
| 58 | phenyl | CH₃ | CH₃ | H | 181–183 | EA: | 55.58 | 4.41 | 20.47 | 55.92 | 4.51 | 20.55 |
| 59 | phenyl | CH₃ | CH₃ | CH₃ | 154–155.5 | EA: | 56.58 | 4.75 | 19.80 | 56.76 | 4.94 | 19.61 |
| 60 | phenyl | CH₃ | CH₃ | OCH₃ | 123–125 | EA: | 54.52 | 4.51 | 19.09 | 54.81 | 4.63 | 19.04 |
| 61 | CONNCH₃ | CH₃ | CH₃ | H | 177–183 | IR(KBr): 3320(Br),3220(Br),3080,3000,1710,1660,1560,1510, 1445,1428,1400,1210,1150,735 cm⁻¹ | | | | | | |

TABLE VII

Physical/Chemical Data for
Heterocyclic-Substituted Thiadiazole Ureas

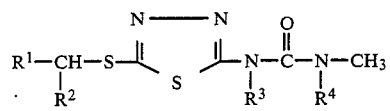

| Compound Number | $R^1$ | $R^2$ | $R^3$ | $R^4$ | Melting Point (°C.) | IR or EA | Calc. C | Calc. H | Calc. N | Found C | Found H | Found N |
|---|---|---|---|---|---|---|---|---|---|---|---|---|
| 62 | quinolin-2-yl | — | H | CH₃ | H | 160–162 (dec.) | IR:(KBr) 3380(Br),3320(Br),3055,2945,2915,1655, 1599,1535,1500,1465,1400,1315,1295, 1200,1180,1156,1099,1065,1050,900, 820,770,755,640,615 cm⁻¹ | | | | | | |
| 63 | quinolin-2-yl | | H | H | H | 151 (dec.) | IR:(KBr) 3320(Br),3060,3000,2940,1665,1595, 1582,1560,1530(Br),1475(Br),1432,1400, 1320,1300,1210,1153,1100,1050,990, 890,752,630,622 cm⁻¹ | | | | | | |
| 64 | 4-chloroquinolin-2-yl | | H | CH₃ | H | 153–155 | 990,899,752,636,622 cm⁻¹ | | | | | | |

TABLE VII-continued

Physical/Chemical Data for
Heterocyclic-Substituted Thiadiazole Ureas

| | | | | | | | | | | | | |
|---|---|---|---|---|---|---|---|---|---|---|---|---|
| 65 | 1,3-benzothiazol-2-yl | H | CH₃ | H | 142-5-143.5 | EA: | 44.43 | 3.73 | 19.93 | 44.66 | 3.95 | 19.61 |
| 66 | 4-phenyl-1,3,4-oxadizaol | H | CH₃ | H | 164-164.5 | EA: | 46.40 | 3.89 | 23.19 | 46.41 | 3.93 | 23.40 |
| 67 | furan-2-yl | H | CH₃ | H | 126.5-128.5 | IR:(KBr) | 3325,3125,2100,1660,1530,1495,1460, 1410,1315,1295,1250,1240,1200,1150, 1135,1095,1055,1000,930,895,880,810, 800,715,690,630 cm⁻¹ | | | | | |
| 68 | 6-chloro-1,3 benzooxazol-2-yl | CH₃ | CH₃ | H | oil | EA: | 43.80 | 3.68 | 18.24 | 43.77 | 3.83 | 17.95 |
| 69 | 2-benzofuran-2-yl | CH₃ | CH₃ | H | 48-52 | EA: | 51.71 | 4.63 | 16.08 | 51.58 | 4.80 | 15.60 |

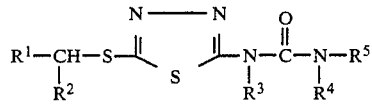

$$R^1-\underset{R^2}{\underset{|}{CH}}-S-\underset{S}{\overset{N\text{---}N}{\underset{\diagdown\diagup}{\|\quad\|}}}-\underset{R^3}{\underset{|}{N}}-\overset{O}{\overset{\|}{C}}-\underset{R^4}{\underset{|}{N}}-R^5$$

| Compound Number | R¹ | R² | R³ | R⁴ | R⁵ | Melting Point (°C.) | Infra-red Spectrum (IR) or Elemental Analysis (EA) | | | | | |
|---|---|---|---|---|---|---|---|---|---|---|---|---|
| | | | | | | | Calc. | | | Found | | |
| | | | | | | | C | H | H | C | H | N |
| 70 | 3-methyl-1,2,4 oxadiazol-5-yl | H | CH₃ | CH₃ | CH₃ | oil | EA: 28.20 | 4.49 | 26.73 | 38.05 | 4.48 | 26.87 |
| 71 | 3-(p-chlorophenyl) 1,2,4-oxadiazol 5-yl | H | CH₃ | CH₃ | H | 178-181 | IR(KBr): 3300,2940,1660,1585,1560,1535,1470, 1400,1340,1310,1300,1205,1280,1005, 895,835,750,635 cm⁻¹ | | | | | |
| 72 | tetrahydro- furan-2-yl | H | CH₃ | CH₃ | H | 96-98 | EA: 41.65 | 5.60 | 19.43 | 41.85 | 5.82 | 19.30 |
| 73 | 2-methyl-1,3- thiazol-4-yl | H | CH₃ | CH₃ | CH₃ | oil | EA: 36.34 | 4.27 | 25.43 | 35.91 | 4.43 | 25.07 |
| 74 | 5-methyl-1,3,4- thiadiazol-2-yl | H | CH₃ | CH₃ | H | 168-170 | EA: 36.16 | 3.82 | 26.56 | 34.51 | 3.90 | 26.84 |
| 75 | 5-methyl-1,3,4- thiadiazol-2-yl | H | CH₃ | CH₃ | CH₃ | oil | EA: 36.34 | 4.27 | 25.43 | 35.91 | 4.43 | 25.07 |
| 76 | phthalimid-n-yl | H | CH₃ | CH₃ | H | 209-213.5 | EA: 46.27 | 3.60 | 19.27 | 45.98 | 3.72 | 19.14 |
| 77 | benzo(b)thien-3-yl | H | CH₃ | CH₃ | H | 147-152.5 | EA: 47.98 | 4.03 | 15.99 | 48.96 | 4.42 | 15.21 |
| 78 | benzo(c)thien-2-yl | H | CH₃ | CH₃ | CH₃ | 102-105 | IR(KBr): 2960,2910,1650,1485,1370,1305,1260, 1120,1090,1050,795,680 cm⁻¹ | | | | | |
| 79 | 4,5-benzo-1,3- oxazolidin-6-one | H | CH₃ | CH₃ | H | 173-175 | EA: 46.27 | 3.60 | 19.27 | 46.37 | 36.63 | 19.24 |
| 80 | 4,5-benzo-1,3- oxazolidin-6-one | H | CH₃ | CH₃ | CH₃ | 135-138 | EA: 47.73 | 4.01 | 18.56 | 47.45 | 4.25 | 18.15 |
| 81 | 4,5-benzo-1,3- diazolidin-6-one | H | CH₃ | CH₃ | H | 205-206 | EA: 46.39 | 3.89 | 23.19 | 27.27 | 4.13 | 22.72 |
| 82 | pyrimidinyl | H | CH₃ | CH₃ | CH₃ | oil | IR(neat): 2950,1660,1480,1450,1405,1370,1310, 1275,1125,1055,1015,690 cm⁻¹ | | | | | |

The biological efficacy of compounds representative of this invention as terrestrial herbicides were evaluated as preemergence herbicides and postemergence herbicides. The test plants were mustard, nightshade, teaweed, velvetleaf and morninglory. For the preemergence test, seeds of the type of plants as shown in Table IV were sown in fresh soil. In the preemergence test, the soil was sprayed with a solution of the test compound immediately after the seeds were planted. The solution was about a 1% by weight solution of the test compound in acetone. The compounds were applied at the rate of 8 lbs/acre of soil surface.

Approximately three weeks after spray applications, the herbicidal activity of the compound was determined by visual observation of the treated areas in comparison with untreated controls. These observations are reported on a scale of 0 to 100% control of plant growth.

In the postemergence test the soil and developing plants were sprayed about two weeks after the seeds were sown. Except where indicated otherwise the compounds were applied at the rate of 8 lbs/acre from about a 1% by weight solution of the test compound in acetone. The postemergence herbicidal activity was measured in the same way as the preemergence activity at three weeks following treatment.

The results of both the preemergence and postemergence tests are set forth in Tables VIII and IX below wherein the compound numbers are the same as those in Tables I-VII and wherein a dash (-) indicates that the compound was not tested against that particular plant.

TABLE VIII

Pre-Emergent Herbicidal Activity of Thiadiazole Ureas

| | Pre-Emergent Activity (% Control) | | | | |
|---|---|---|---|---|---|
| Compound Number | Morning Glory | Velvet Leaf | Mustard | Night- shade | Teaweed |
| 1 | 0 | 97 | 100 | 100 | — |
| 2 | 100 | 100 | 100 | 100 | — |
| 3 | 42 | 100 | 100 | 100 | 100 |
| 4 | 100 | 100 | 100 | 100 | 100 |
| 5 | 100 | 100 | 100 | 100 | 100 |
| 6 | 0 | 0 | 0 | 0 | — |
| 7 | 0 | 0 | 0 | 0 | — |
| 8 | 56 | 54 | 100 | 38 | 100 |
| 10 | 30 | 100 | 100 | 100 | — |
| 11 | 62 | 50 | 100 | 33 | 22 |
| 12 | 20 | 100 | 100 | 0 | — |
| 13 | 0 | 0 | 20 | 100 | 6 |
| 14 | 0 | 0 | 72 | 0 | — |
| 15 | 100 | 100 | 100 | 100 | 100 |
| 17 | 99 | 100 | 100 | 74 | 6 |
| 18 | 100 | 100 | 100 | 100 | 100 |
| 19 | 0 | 0 | 0 | 0 | — |
| 20 | 0 | 0 | 100 | 0 | 43 |
| 21 | 55 | 12 | 100 | 20 | 100 |
| 22 | 100 | 100 | 100 | 100 | 100 |
| 23 | 100 | 100 | 100 | 100 | 100 |

TABLE VIII-continued

Pre-Emergent Herbicidal Activity of Thiadiazole Ureas

| Compound Number | Pre-Emergent Activity (% Control) | | | | |
|---|---|---|---|---|---|
| | Morning Glory | Velvet Leaf | Mustard | Nightshade | Teaweed |
| 24 | 0 | 0 | 0 | 0 | — |
| 25 | 0 | 0 | 0 | 0 | — |
| 26 | 0 | 0 | 20 | 6 | — |
| 27 | 12 | 12 | 0 | 0 | — |
| 29 | 12 | 0 | 0 | 0 | — |
| 30 | 100 | 100 | 100 | 100 | 100 |
| 31 | 65 | 100 | 100 | 100 | 100 |
| 32 | 100 | 100 | 100 | 100 | 100 |
| 33 | 100 | 100 | 100 | 0 | 100 |
| 34 | 100 | 100 | 100 | 0 | 12 |
| 35 | 100 | 100 | 100 | 100 | 100 |
| 36 | 100 | 100 | 100 | 100 | 100 |
| 37 | 100 | 100 | 100 | 100 | 100 |
| 38 | 100 | 100 | 100 | 100 | 100 |
| 39 | 100 | 100 | 100 | 100 | 100 |
| 40 | 74 | 100 | 100 | — | 100 |
| 41 | 100 | 100 | 100 | 100 | 100 |
| 42 | 100 | 100 | 100 | 100 | 100 |
| 43 | — | 100 | 100 | 100 | 100 |
| 45 | 100 | 100 | 100 | 100 | 100 |
| 46 | 6 | 0 | 100 | 0 | 6 |
| 47 | 54 | 62 | 56 | 100 | 0 |
| 48 | 0 | — | 0 | — | — |
| 51 | 20 | — | 100 | — | — |
| 52 | 100 | — | 100 | — | — |
| 53 | 100 | 100 | 20 | 100 | 100 |
| 54 | 0 | 0 | 0 | 100 | 100 |
| 55 | 100 | 100 | 100 | 100 | 43 |
| 57 | 88 | 100 | 100 | 100 | 100 |
| 59 | 0 | 0 | 100 | 0 | 0 |
| 61 | 0 | 12 | 20 | 0 | 0 |
| 62 | — | 0 | 0 | 0 | — |
| 63 | 0 | 0 | 0 | 0 | — |
| 64 | 0 | 0 | 6 | 0 | 0 |
| 65 | 100 | 100 | 100 | 100 | 100 |
| 66 | 100 | 22 | 80 | 100 | 100 |
| 67 | 99 | 100 | 100 | 100 | 100 |
| 68 | 100 | 12 | 100 | 100 | 73 |
| 69 | 100 | 100 | 100 | 100 | 100 |
| 70 | 100 | — | 100 | — | — |
| 71 | 0 | 30 | 12 | — | 0 |
| 72 | 100 | 100 | 100 | — | 100 |
| 73 | 100 | — | 100 | — | — |
| 74 | 100 | 100 | 100 | 100 | 100 |
| 75 | 100 | — | 100 | — | — |
| 76 | 6 | 0 | 0 | 0 | 0 |
| 77 | 0 | 0 | 100 | 0 | 40 |
| 78 | 100 | 100 | 100 | 100 | 32 |
| 79 | 0 | 0 | 12 | 100 | 0 |

TABLE IX

Post-Emergent Herbicidal Activity of Thiadiazole Ureas

| Compound Number | Post-Emergent Activity (% Control) | | | | |
|---|---|---|---|---|---|
| | Morning Glory | Velvet Leaf | Mustard | Nightshade | Teaweed |
| 1 | 40 | 100 | 100 | 100 | — |
| 2 | 100 | 100 | 100 | 100 | — |
| 3 | 98 | 100 | 100 | 100 | — |
| 4 | 100 | 100 | 100 | 100 | 100 |
| 5 | 100 | 100 | 100 | 100 | 100 |
| 6 | 35 | 100 | 100 | 100 | — |
| 7 | 100 | 100 | 100 | 100 | 100 |
| 8 | 100 | 100 | 100 | 100 | 100 |
| 10 | 100 | 100 | 100 | 100 | — |
| 11 | 100 | 80 | 100 | 80 | 100 |
| 12 | 42 | 74 | 100 | 14 | 0 |
| 13 | 0 | 100 | 100 | 100 | 100 |
| 14 | 100 | 100 | 100 | 100 | 0 |
| 15 | 100 | 100 | 100 | 100 | 100 |
| 17 | 100 | 100 | 100 | 100 | 100 |
| 18 | 100 | 100 | 100 | 100 | 100 |
| 19 | 0 | 0 | 0 | 0 | 0 |
| 20 | 12 | 0 | 65 | 0 | 10 |
| 21 | 10 | 0 | 50 | 20 | 70 |
| 22 | 33 | 100 | 100 | 100 | 100 |
| 23 | 100 | 100 | 100 | 100 | 100 |
| 24 | 20 | 100 | 100 | 100 | 0 |
| 25 | 20 | 100 | 100 | 100 | 0 |
| 26 | 19 | 100 | 100 | 100 | 0 |
| 29 | 0 | 12 | 10 | 0 | 12 |
| 30 | 0 | 100 | 100 | 100 | 100 |
| 31 | 100 | 100 | 100 | 100 | 100 |
| 32 | 100 | 100 | 100 | — | 100 |
| 33 | 100 | 100 | 100 | — | 100 |
| 34 | — | 100 | 100 | — | 77 |
| 35 | 100 | 100 | 100 | 100 | 100 |
| 36 | 100 | 100 | 100 | 100 | 100 |
| 37 | 100 | 100 | 100 | 100 | 100 |
| 38 | 12 | 55 | 100 | 100 | 100 |
| 39 | 100 | 100 | 100 | 100 | 100 |
| 40 | 100 | 100 | 100 | 100 | 100 |
| 41 | 100 | 100 | 100 | — | 100 |
| 42 | 100 | 100 | 100 | 100 | 100 |
| 43 | 100 | 100 | 100 | 100 | 100 |
| 45 | 100 | 100 | 100 | 100 | 100 |
| 46 | 45 | 0 | 30 | 0 | — |
| 47 | 0 | 100 | 98 | 100 | 98 |
| 48 | 0 | — | 20 | — | — |
| 51 | 100 | — | 100 | — | — |
| 52 | 100 | — | 100 | — | — |
| 53 | 100 | 100 | 100 | 100 | 100 |
| 54 | 100 | 100 | 100 | 100 | 100 |
| 55 | 100 | 100 | 100 | 100 | 100 |
| 57 | 87 | 100 | 100 | 100 | 86 |
| 58 | — | 0 | 97 | 0 | 0 |
| 59 | — | 85 | 100 | 100 | 60 |
| 60 | 0 | 0 | 54 | — | 0 |
| 61 | 22 | 100 | 100 | 100 | — |
| 62 | 100 | 100 | 100 | 100 | 100 |
| 63 | 40 | 100 | 100 | 100 | — |
| 64 | 6 | 0 | 100 | 100 | 84 |
| 65 | 70 | 100 | 100 | 100 | 100 |
| 66 | 0 | 53 | 100 | 100 | 40 |
| 67 | 100 | 100 | 100 | 100 | 100 |
| 68 | 100 | 100 | 100 | 100 | 100 |
| 69 | 100 | 100 | 100 | 100 | 100 |
| 70 | 100 | — | 100 | — | — |
| 71 | 62 | 100 | 82 | — | 62 |
| 72 | 100 | 100 | 100 | — | 100 |
| 73 | 100 | — | 100 | — | — |
| 74 | 100 | 100 | 100 | 100 | 100 |
| 75 | 100 | — | 100 | — | — |
| 77 | 100 | 100 | 100 | 100 | 100 |
| 78 | — | 100 | 100 | — | 100 |

The data presented in Tables VIII and IX show that the compounds of this invention having pyridinyl, thienyl, furanyl, benzofuranyl, benzothiazolyl or thiadiazolyl substituents generally have excellent herbicidal activities.

Representative compounds of this invention were tested for phytotoxicity to corn, soybeans, wheat and cotton. The compounds were applied to the subject plants as indicated for the herbicide tests with the exception that the compounds were applied at a rate of 0.5 lbs per acre. The results of the phytotoxicity tests for both pre-emergent and post-emergent application, in terms of percent kill wherein a dash indicates no test, are shown in Tables X, XI below.

TABLE X

Pre-Emergent Phytotoxicity

| Compound Number | Soybean | Corn | Wheat | Cotton |
|---|---|---|---|---|
| 1 | — | — | — | — |
| 2 | — | — | — | — |
| 3 | — | — | — | — |
| 4 | — | 0 | 0 | 7 |
| 5 | — | 0 | — | 100 |
| 6 | — | — | — | — |
| 7 | — | — | — | — |
| 8 | — | — | 0 | 100 |
| 9 | — | 0 | — | 42 |
| 10 | — | — | — | — |
| 11 | — | 0 | 0 | 75 |
| 12 | — | 0 | 0 | 0 |
| 13 | — | — | — | — |
| 14 | — | — | — | — |
| 15 | 100 | — | — | 100 |
| 16 | — | 0 | 10 | 42 |
| 17 | 0 | 0 | 0 | 67 |
| 18 | — | 0 | 90 | 100 |
| 19 | — | — | — | — |
| 20 | — | — | — | — |
| 21 | — | — | — | — |
| 22 | 11 | 0 | 0 | 95 |
| 23 | — | 0 | 0 | 11 |
| 24 | — | — | — | — |
| 25 | — | — | — | — |
| 26 | — | — | — | — |
| 27 | — | — | — | — |
| 28 | — | — | — | — |
| 29 | — | — | — | — |
| 30 | — | 0 | 0 | 100 |
| 31 | 0 | 0 | 0 | 94 |
| 32 | 0 | 0 | 11 | 100 |
| 33 | 0 | 0 | 0 | 100 |
| 34 | — | 0 | 0 | 11 |
| 35 | — | 0 | 0 | 1 |
| 36 | — | 0 | 0 | 1 |
| 37 | — | 0 | 0 | 100 |
| 38 | — | — | — | — |
| 39 | 0 | 0 | 0 | 0 |
| 40 | 0 | 0 | 0 | 95 |
| 41 | 0 | 0 | 0 | 100 |
| 42 | — | 0 | 0 | 55 |
| 43 | 0 | 0 | 0 | 0 |
| 44 | — | — | — | — |
| 45 | — | 0 | 10 | 100 |
| 46 | — | — | — | — |
| 47 | — | — | — | — |
| 48 | — | — | — | — |
| 49 | — | — | — | — |
| 50 | — | — | — | — |
| 51 | 6 | 0 | 0 | 0 |
| 52 | — | — | — | — |
| 53 | — | 0 | 0 | 100 |
| 54 | — | 0 | 0 | 0 |
| 55 | 0 | 0 | 0 | 1 |
| 56 | — | — | — | — |
| 57 | — | 0 | 0 | 0 |
| 58 | — | 0 | 0 | 0 |
| 59 | — | 0 | 0 | 0 |
| 60 | — | 0 | 0 | 0 |
| 61 | — | — | — | — |
| 62 | — | — | — | — |
| 63 | — | — | — | — |
| 64 | — | — | — | — |
| 65 | — | 0 | 0 | 32 |
| 66 | — | 0 | 0 | 0 |
| 67 | — | 0 | 0 | 1 |
| 68 | — | 0 | 0 | 1 |
| 69 | 0 | 0 | 0 | 26 |
| 70 | 78 | 12 | 62 | 100 |
| 71 | — | 0 | 6 | 0 |
| 72 | 0 | 0 | 0 | 32 |
| 63 | 7 | 6 | 0 | 58 |
| 74 | — | — | — | — |
| 75 | 100 | 71 | 100 | 100 |
| 76 | — | 0 | 0 | 0 |
| 77 | — | 0 | 0 | 1 |
| 78 | — | — | — | — |
| 79 | — | — | — | — |
| 80 | — | — | — | — |
| 81 | — | — | — | — |
| 82 | — | — | — | — |

TABLE XI

Post-Emergent Phytotoxicity

| Compound Number | Soybean | Corn | Wheat | Cotton |
|---|---|---|---|---|
| 1 | — | — | — | — |
| 2 | — | — | — | — |
| 3 | — | — | — | — |
| 4 | 0 | 0 | 0 | 7 |
| 5 | 1 | 0 | — | 100 |
| 6 | — | — | — | — |
| 7 | — | — | — | — |
| 8 | 21 | 0 | — | — |
| 9 | 0 | 0 | 10 | 42 |
| 10 | — | — | — | — |
| 11 | 0 | 0 | 0 | 75 |
| 12 | 0 | 0 | 0 | 0 |
| 13 | — | — | — | — |
| 14 | — | — | — | — |
| 15 | 40 | 0 | 20 | 100 |
| 16 | 0 | 0 | 10 | 42 |
| 17 | 1 | 0 | 0 | 74 |
| 18 | 11 | 0 | 90 | 100 |
| 19 | — | — | — | — |
| 20 | — | — | — | — |
| 21 | — | — | — | — |
| 22 | 0 | 0 | 0 | 94 |
| 23 | 11 | 0 | 0 | 11 |
| 24 | — | — | — | — |
| 25 | — | — | — | — |
| 26 | — | — | — | — |
| 27 | — | — | — | — |
| 28 | — | — | — | — |
| 29 | — | — | — | — |
| 30 | 0 | 0 | 0 | 100 |
| 31 | 11 | 0 | 0 | 94 |
| 32 | 0 | 0 | 11 | 100 |
| 33 | 0 | 0 | 0 | 100 |
| 34 | 0 | 0 | 0 | 11 |
| 35 | 0 | 0 | 0 | 1 |
| 36 | 0 | 0 | 0 | 1 |
| 37 | 0 | 0 | 0 | 100 |
| 38 | — | — | — | — |
| 39 | 0 | 0 | 0 | 0 |
| 40 | 0 | 0 | 0 | 95 |
| 41 | 0 | 0 | 0 | 100 |
| 42 | 0 | 0 | 0 | 55 |
| 43 | 0 | 0 | 0 | 0 |
| 44 | 19 | 0 | 0 | 100 |
| 45 | 0 | 0 | 10 | 100 |
| 46 | — | — | — | — |
| 47 | — | — | — | — |
| 48 | — | — | — | — |
| 49 | 100 | 0 | — | 100 |
| 50 | 0 | 0 | 0 | 0 |
| 51 | 15 | 0 | 0 | 100 |
| 52 | 100 | 32 | 40 | 100 |
| 53 | 1 | 0 | 0 | 100 |
| 54 | 1 | 0 | 0 | 0 |
| 55 | 0 | 0 | 0 | 1 |
| 56 | — | — | — | — |
| 57 | 0 | 0 | 0 | 0 |
| 58 | 0 | 0 | 0 | 0 |
| 59 | 0 | 0 | 0 | 0 |
| 60 | 0 | 0 | 0 | 0 |
| 61 | — | — | — | — |
| 62 | — | — | — | — |
| 63 | — | — | — | — |
| 64 | — | — | — | — |
| 65 | 0 | 0 | 0 | 32 |
| 66 | 0 | 0 | 0 | 0 |
| 67 | 0 | 0 | 0 | 1 |

TABLE XI-continued

| Compound Number | Post-Emergent Phytotoxicity | | | |
|---|---|---|---|---|
| | Soybean | Corn | Wheat | Cotton |
| 68 | 0 | 0 | 0 | 1 |
| 69 | 0 | 0 | 0 | 14 |
| 70 | 6 | 0 | 10 | 35 |
| 71 | 0 | 0 | 0 | 0 |
| 72 | 11 | 0 | 0 | 24 |
| 73 | 10 | 0 | 10 | 36 |
| 74 | — | — | — | — |
| 75 | 100 | 0 | 66 | 96 |
| 76 | 0 | 0 | 0 | 0 |
| 77 | 0 | 0 | 0 | 1 |
| 78 | — | — | — | — |
| 79 | — | — | — | — |
| 80 | — | — | — | — |
| 81 | — | — | — | — |
| 82 | 20 | 0 | 0 | 14 |

The data in Tables X and XI show that the compounds of this invention generally do not injure important organic crops. The notable exceptions are the compounds with isoxazolyl substituents which possess excellent broad spectrum activity but are generally not selective toward soybeans.

It will be understood that the plant species employed in the above tests are merely representative of a wide variety of plants that can be controlled by the use of the compounds of this invention. The compounds contemplated in this invention may be applied as postemergent and preemergent herbicides according to methods known to those skilled in the art. Compositions containing the compounds as the active ingredient will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agent.

The choice of dispersing and emulsifying agents and the amount employed is dictated by the nature of the composition and the ability of the agent to facilitate the dispersion of the compound. Generally, it is desirable to use as little of the agent as is possible, consistent with the desired dispersion of the compound in the spray so that rain does not re-emulsify the compound after it is applied to the plant and wash it off the plant. Nonionic, anionic, amphoteric or cationic dispersing and emulsifying agents may be employed; for example, the condensation products of alkylene oxides with phenol and organic acids, alkyl aryl sulfonates, complex ether alcohols, quaternary ammonium compounds, and the like.

Activities per pound of active ingredient can be increased by the use of an emulsifiable crop oil. A proprietary composition sold by Union Carbide Corporation under its registered trademark SURFEL and which is a phytobland mixture of surfactant and oil is particularly suitable. The surfactant is a blend of polyoxyethylene ethers and the oil is a paraffinic petroleum distillate.

In the preparation of wettable powder or dust or granulated compositions, the active ingredient is dispersed in and on an appropriately divided solid carrier such as clay, talc, bentonite, diatomaceous earth, fullers earth, and the like. Dispersing agents as well as lignosulfonates can be included in the formulation of the wettable powders.

An effective herbicidal amount of a herbicidal compound according to this invention can be applied in quantities of from 1 to 200 gallons or more of liquid carrier and/or diluent or in from about 5 to 500 pounds of inert solid carrier and/or diluent per acre. The concentration of herbicidal compound in the liquid concentrate will usually vary from about 10 to 95 percent by weight and in the solid formulations from about 0.5 to about 90 percent by weight. Satisfactory sprays, dusts, or granules for general use contain from about 1/4 to 15 pounds of active ingredient per acre.

The herbicides contemplated herein have a high margin of safety in that when used in sufficient amount to control broadleaf weeds they do not burn or injure the crop. It will be appreciated that the compounds of this invention can also be used in combination with other biologically active compounds.

What is claimed is:

1. Compounds having the structural formula:

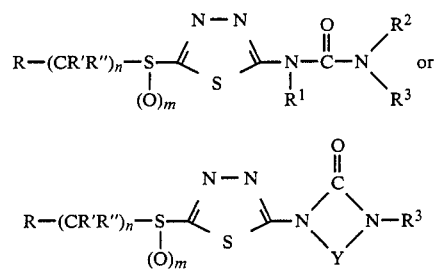

wherein
R is:
(a) a substituted or unsubstituted radical having the structural formula:

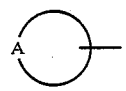

wherein A is an alkylene or alkenylene chain having 5, 6 or 7 ring members which are replaced by one to three heteroatoms, in any location and in any combination, selected from the groups of oxygen, nitrogen and sulfur, wherein the permissible substituents are one or more alkyl, alkoxy, carboalkoxy, monoalkylamino, dialkylamino, amido, alkylthio, phenyl, halogen, trihalomethyl hydroxy, cyano, mercapto or nitro substituents provided that any substituent may not have more than eight aliphatic carbon atoms: or (b) a substituted or unsubstituted radical having a structural formula:

wherein A is as defined above and A' is an alkylene or alkenylene chain having 3, 4 or 5 members which may be replaced by up to three hetero atoms, in any location and in any combination, selected from the group of oxygen, nitrogen and sulfur, or A' is a 4-membered polyunsaturated chain, wherein the permissible substituents are one or more alkyl, alkoxy, carboalkoxy, monoalkylamino, dialkylamino, amido, alkylthio, phenyl, halogen, trihalomethyl hydroxy, cyano, mercapto or nitro substituents;

R' and R" are independently hydrogen, alkyl, cycloalkyl, alkoxy, carboalkoxy or halogen, provided that R' and R" independently may not contain more than four carbon atoms;

n is an integer from 1 to 5;

m may be 0, 1 or 2

$R^1$, $R^2$ and $R^3$ are independently hydrogen, cylopentyl, cyclohexyl, cyclopropyl, phenyl, alkyl or alkoxy each containing no more than eight carbon atoms; and Y is a substituted or unsubstituted divalent alkylene or alkenylene chain having two or three members wherein any one carbon atom in said chain may be replaced with an amino group and any one or two carbon atoms in said chain may be replaced with a carbonyl group, and wherein the permissible substituents are one or more halo, alkoxy or hydroxy.

2. A compound in accordance to claim 1 wherein R is a monocyclic heterocyclic radical having 5 ring members.

3. A compound in accordance to claim 1 wherein R is a monocyclic heterocyclic radical having 6 ring members.

4. A compound in accordance to claim 1 wherein R is a 6,6-bicyclic heterocyclic radical.

5. A compound in accordance to claim 1 wherein R is a 5,6-bicyclic heterocyclic radical.

6. A compound in accordance to claim 1 having the structural formula:

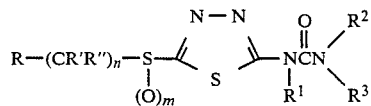

wherein $R^1$, $R^2$ and $R^3$ are independently hydrogen, alkyl or alkoxy.

7. A compound in accordance with claim 1 wherein Y is —CH$_2$—CH(OH)—, —CH=CH—, —CO—CH$_2$—, —CH—N(CH$_3$)— or —CO—CO—.

8. A compound in accordance with claim 1 wherein n is 1 or 2 and m is zero.

9. A compound in accordance with claim 1 wherein n is 1 or 2, m is zero, R' and R" are hydrogen and $R^1$ is methyl or ethyl.

10. A compound in accordance with claim 1 wherein n is 1 or 2, m is zero, R' and R" are hydrogen, $R^1$ and $R^2$ are methyl, $R^3$ is hydrogen or methyl.

11. A compound in accordance with claim 10 wherein R is pyridinyl.

12. A compound in accordance with claim 10 wherein R is isoxazolyl.

13. A compound in accordance with claim 10 wherein R is benzoimidazolyl, benzothiazolyl, benzooxazolyl, benzofuranyl, or benzothienyl.

14. A compound in accordance with claim 10 wherein R is furanyl or thienyl.

15. A compound in accordance with claim 10 wherein R is thiadiazolyl.

16. 1,3-dimethyl-3[5(6-chloropyrid-2-yl)methylthio-1,3,4-thiadiazol-2-yl]urea.

17. 1,1,3-trimethyl-3-[5-(2-(thien-2-yl)ethylthio)-1,3,4-thiadiazol-2-yl]urea.

18. 1,3-dimethyl-3-[5-(3-methylisoxazol-5-yl)methylthio-1,3,4-thiadiazol-2-yl]urea.

19. 1-[5-thien-2-yl)methylthio-1,3,4-thiadiazol-2-yl]-2-hydroxy-4-methyl-imidazolinoneurea.

20. A herbicidal composition comprising an acceptable carrier and a herbicidally effective amount of the herbicidal compound of claim 1.

21. A composition in accordance with claim 20 wherein the herbicidal compound is 1,3-dimethyl-3-[5(6-chloropyrid-2-yl)methylthio-1,3,4-thiadiazol-2-yl]urea.

22. A composition in accordance with claim 20 wherein the herbicidal compound is 1,1,3-trimethyl-3-[5-(2-thien-2-yl)ethylthio)-1,3,4-thiadiazol-2-yl]urea.

23. A composition in accordance with claim 20 wherein the herbicidal compound is 1,3-dimethyl-3-[5-(thien-2-yl)methylthio-1,3,4-thiadiazol-2-yl]urea.

24. A method for the selective control of undesirable vegetation which comprises applying a herbicidally effective amount of the compound of claim 1.

25. A method in accordance with claim 24 wherein the compound is 1,3-dimethyl-3-[5(6-chloropyrid-2-yl)methylthio-1,3,4-thiadiazol-2-yl]urea.

26. A method in accordance with claim 24 wherein the compound is 1,1,3-trimethyl-3-[5-(2-thien-2-yl)ethylthio)-1,3,4-thiadiazol-2-yl]urea.

27. A method in accordance with claim 24 wherein the compound is 1,3-dimethyl-3-[5-(thien-2-yl)methylthio-1,3,4-thiadiazol-2-yl]urea.

28. A process for the preparation of a compound having a structural formula in accordance to claim 1:

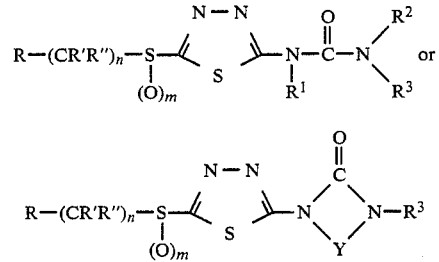

which comprises:

(a) reacting a compound having the structural formula:

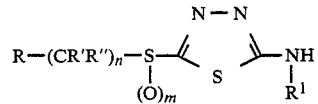

with at least a stoichiometric amount of phosgene gas or 1,1'-carbonyldiimidazole, and (b) reacting the resulting product from step (a) with an amine having the formula $R^2NR^3$

wherein
R is:

(a) a substituted or unsubstituted radical having the structural formula:

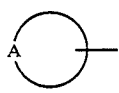

wherein A is an alkylene or alkenylene chain having 5, 6 or 7 ring members which are replaced by one to three heteroatoms, in any location and in any combination, selected from the groups of oxygen, nitrogen and sulfur, wherein the permissible substituents are one or more alkyl, alkoxy, carboalkoxy, monoalkylamino, dialkylamino, amido, alkylthio, phenyl, halogen, trihalomethyl hydroxy, cyano, mercapto or nitro substituents provided that any substituent may not have more than eight aliphatic carbon atoms: or (b) a substituted or unsubstituted radical having a structural formula:

wherein A is as defined above and A' is an alkylene or alkenylene chain having 3, 4 or 5 members which may be replaced by up to three hetero atoms, in any location and in any combination, selected from the group of oxygen, nitrogen and sulfur, or A' is a 4-membered polyunsaturated chain, wherein the permissible substituents are one or more alkyl, alkoxy, carboalkoxy, monoalkylamino, dialkylamino, amido, alkylthio, phenyl, halogen, trihalomethy hydroxy, cyano, mercapto or nitro substituents;

R' and R" are independently hydrogen, alkyl, cycloalkyl, alkoxy, carboalkoxy or halogen, provided that R' and R" independently may not contain more than four carbon atoms;

n is an integer from 1 to 5;

m may be 0, 1 or 2

$R^1$, $R^2$ and $R^3$ are independently hydrogen, cyclopentyl, cyclohexyl, cyclopropyl, phenyl, alkyl or alkoxy each containing no more than eight carbon atoms; and Y is a substituted or unsubstituted divalent alkylene or alkenylene chain having two or three members wherein any one carbon atom in said chain may be replaced with an amino group and any one or two carbon atoms in said chain may be replaced with a carbonyl group, and wherein the permissible substituents are one or more halo, alkoxy or hydroxy.

* * * * *

UNITED STATES PATENT AND TRADEMARK OFFICE
CERTIFICATE OF CORRECTION

PATENT NO. : 4,576,629

DATED : March 18, 1986

INVENTOR(S) : Robert B. Morland, Anson R. Cooke and John R. Bishop

It is certified that error appears in the above-identified patent and that said Letters Patent is hereby corrected as shown below:

Column 1, line 62, after "ring" change the period to a comma.

Column 2, line 2, change "structrual" to --structural--.

Column 2, lines 47-48, change "naphtyl" to --naphthyl--.

Column 6, line 35, change "thiadizole" to --thiadiazole--.

Column 7, line 26, remove the spaces between "thia" and "diazol".

Column 7, line 32, change the "thiadizole" portion of the compound name to --thiadiazole--.

Column 13, line 56, delete the entire line and substitute --1,3-dimethyl-1-ethyl-3-[5-(1-(pyrimidin-2-yl)ethylthio)-1,3,4-thiadiazol-2-yl]urea-- therefor.

Column 14, line 8, change the "thiadizol" portion of the compound name to --thiadiazol--.

Column 14, line 12, change the "thiadizol" portion of the compound name to --thiadiazol--.

Column 14, line 19, change the "thiadizol" portion of the compound name to --thiadiazol--.

Column 14, line 22, change the "thiadizol" portion of the compound name to --thiadiazol--.

Column 14, line 27, delete the "9" and substitute --)--, i.e. a right parenthesis, therefor.

UNITED STATES PATENT AND TRADEMARK OFFICE
CERTIFICATE OF CORRECTION

PATENT NO. : 4,576,629

DATED : March 18, 1986

INVENTOR(S) : Robert B. Morland, Anson R. Cooke and John R. Bishop

It is certified that error appears in the above-identified patent and that said Letters Patent is hereby corrected as shown below:

Column 14, line 40, change the "thiadizol" portion of the compound name to --thiadiazol--.

Column 16, line 25, delete the spaces between the "chloro" and "pyrid" portions of the compound name.

Column 16, line 35, change the "diemthyl" portion of the compound name to --dimethyl--.

Column 22, TABLE VI, in the row for Compound Number 56, change

"EA:  48.82   4.63    46.06   4.94   22.86
              24.12"

to

--EA:  48.82   4.63   24.12   46.06   4.94   22.86--

UNITED STATES PATENT AND TRADEMARK OFFICE
CERTIFICATE OF CORRECTION

PATENT NO. : 4,576,629

DATED : March 18, 1986

INVENTOR(S) : Robert B. Morland, Anson R. Cooke and John R. Bishop

It is certified that error appears in the above-identified patent and that said Letters Patent is hereby corrected as shown below:

Column 24, TABLE VII, in the heading just above the row for compound Number 70, change "$\dfrac{\text{Calc.}}{\text{C} \quad \text{H} \quad \text{H}}$"

to

--$\dfrac{\text{Calc.}}{\text{C} \quad \text{H} \quad \text{N}}$--

Signed and Sealed this

Twenty-ninth Day of September, 1987

Attest:

DONALD J. QUIGG

Attesting Officer   Commissioner of Patents and Trademarks